US008394354B2

(12) United States Patent
Paige et al.

(10) Patent No.: US 8,394,354 B2
(45) Date of Patent: Mar. 12, 2013

(54) BIOMARKERS FOR DEPRESSION AND METHODS USING THE SAME

(75) Inventors: Lisa A. Paige, Hillsborough, NC (US); Matthew W. Mitchell, Durham, NC (US); Anne Evans, Durham, NC (US); Don Harvan, Durham, NC (US); David Carl Steffens, Durham, NC (US); K. Ranga R. Krishnan, Chapel Hill, NC (US); Rima Kaddurah-Daouk, Belmont, MA (US)

(73) Assignees: Metabolon, Inc., Durham, NC (US); Duke University, Durham, NC (US)

( * ) Notice: Subject to any disclaimer, the term of this patent is extended or adjusted under 35 U.S.C. 154(b) by 667 days.

(21) Appl. No.: 12/300,000

(22) PCT Filed: May 8, 2007
(Under 37 CFR 1.47)

(86) PCT No.: PCT/US2007/068438
§ 371 (c)(1),
(2), (4) Date: May 27, 2009

(87) PCT Pub. No.: WO2007/134028
PCT Pub. Date: Nov. 22, 2007

(65) Prior Publication Data
US 2010/0197626 A1 Aug. 5, 2010

Related U.S. Application Data

(60) Provisional application No. 60/799,080, filed on May 9, 2006.

(51) Int. Cl.
*G01N 33/49* (2006.01)
*G01N 33/50* (2006.01)
*G01N 33/64* (2006.01)

(52) U.S. Cl. .............................. 424/9.1; 702/19; 702/23

(58) Field of Classification Search ..................... None
See application file for complete search history.

(56) References Cited

U.S. PATENT DOCUMENTS

| 7,005,255 | B2 | 2/2006 | Kaddurah-Daouk et al. |
| 2002/0127623 | A1 | 9/2002 | Minshull et al. |
| 2005/0014132 | A1 | 1/2005 | Kaddurah-Daouk et al. |
| 2006/0134676 | A1 | 6/2006 | Kaddurah-Daouk et al. |
| 2006/0134677 | A1 | 6/2006 | Kaddurah-Daouk et al. |
| 2006/0134678 | A1 | 6/2006 | Kaddurah-Daouk et al. |
| 2007/0026389 | A1 | 2/2007 | Kaddurah-Daouk et al. |
| 2007/0072203 | A1 | 3/2007 | Kaddurah-Daouk et al. |

OTHER PUBLICATIONS

Quinones et al., Neurobiology of disease, 35:165-176, 2009.*
Avogaro et al., Journal of Lipid Research, 30(11):1811-17, 1989.*
International Search Report for International Application No. PCT/US2007/068438; International Filing Date: May 8, 2007; Date of Completion: Aug. 16, 2008.
International Preliminary Report on Patentability for International Application No. PCT/US2007/068438; International Filing Date: May 8, 2007; Date of Issuance Nov. 11, 2008.
Dunckley, T. et al., "Discovery and development of biomarkers of neurological disease", Drug Discovery Today, 10(5), 326-334 (2005).

* cited by examiner

*Primary Examiner* — Daniel E Kolker
*Assistant Examiner* — Stacey N MacFarlane
(74) *Attorney, Agent, or Firm* — Brinks Hofer Gilson & Lione

(57) ABSTRACT

The present invention provides various biomarkers of depression. The present invention also provides various methods of using the biomarkers, including methods for diagnosis of depression, methods of determining predisposition to depression, methods of monitoring progression/regression of depression, methods of assessing efficacy of compositions for treating depression, methods of screening compositions for activity in modulating biomarkers of depression, methods of treating depression, as well as other methods based on biomarkers of depression.

18 Claims, No Drawings

BIOMARKERS FOR DEPRESSION AND METHODS USING THE SAME

CROSS-REFERENCE TO RELATED APPLICATION

This application is a National Stage Application of International Application No. PCT/US2007/068438, filed May 8, 2007 which claims the benefit of U.S. Provisional Application No. 60/799,080, filed May 9, 2006, the entire contents of which are hereby incorporated herein by reference.

STATEMENT REGARDING FEDERALLY SPONSORED RESEARCH

This invention was made, in part, with Government support under Grant Nos. P50 MH60451, R01 MH54846, and K24 MH70027 from the National Institute of Mental Health. The U.S. Government may have certain rights in this invention.

FIELD

The invention generally relates to biomarkers for depression and methods based on the same biomarkers.

BACKGROUND

Depression is a serious mental health problem in the United States that has increased in prevalence over the years. Depression is estimated to affect over 17 million Americans each year. The socioeconomic impact of depression is significant; the cost is estimated to be over $44 billion annually. Further, people suffering from depression carry the risk of suicide. Up to 15% of those who are suffering from depression die by suicide. There are 30,000 to 35,000 suicide-related deaths attributed to depression a year, which is a rate similar to the death rate from leukemia.

Currently, depression is diagnosed by verbal tests that must be administered by a mental health professional. The tests rely on self-reports from the subject whereby the subjects verbally describe their feelings or are presented with verbally-described scenarios and select the scenario that best describes their feelings. The clinician then uses these responses to rate the symptoms. The rating scales provide check-lists for clinicians and diagnosticians to monitor patients' responses to treatment or reactions to environmental changes. Measuring treatment efficacy is reliant upon self-reports and verbal tests and evaluations. These tests and evaluations are limited by the reliance on verbal communication from the patient, by the requirement for administration by mental health professionals and by their subjective nature. Further, the tests do not provide a means to predict predisposition to depression.

Primary care providers may not recognize the symptoms of depression. As a result, depression may go un-diagnosed. A need exists for an objective, biochemical evaluation (e.g. lab test) that can be administered by primary care providers.

A wealth of evidence exists that depression results from an imbalance in brain chemistry. This idea has lead to anti-depressive medications based upon the inhibition of the uptake of the neurotransmitters serotonin and epinephrine.

SUMMARY

In one aspect, a method of diagnosing whether a subject has depression is provided. The method comprises:
 analyzing a biological sample from a subject to determine the level(s) of one or more biomarkers for depression in the sample, wherein the one or more biomarkers are selected from Tables 1 and 2; and
 comparing the level(s) of the one or more biomarkers in the sample to depression-positive and/or depression-negative reference levels of the one or more biomarkers in order to diagnose whether the subject has depression.

In another aspect, a method of determining whether a subject is predisposed to developing depression is provided, comprising:
 analyzing a biological sample from a subject to determine the level(s) of one or more biomarkers for depression in the sample, wherein the one or more biomarkers are selected from Tables 1 and 2; and
 comparing the level(s) of the one or more biomarkers in the sample to depression-positive and/or depression-negative reference levels of the one or more biomarkers in order to determine whether the subject is predisposed to developing depression.

In yet another aspect, a method of monitoring progression/regression of depression in a subject is provided. The method comprises:
 analyzing a first biological sample from a subject to determine the level(s) of one or more biomarkers for depression in the sample, wherein the one or more biomarkers are selected from Tables 1, 2, and 3 and the first sample is obtained from the subject at a first time point;
 analyzing a second biological sample from a subject to determine the level(s) of the one or more biomarkers, wherein the second sample is obtained from the subject at a second time point; and
 comparing the level(s) of one or more biomarkers in the first sample to the level(s) of the one or more biomarkers in the second sample in order to monitor the progression/regression of depression in the subject.

In a further aspect, a method of assessing the efficacy of a composition for treating depression is provided. The method comprises:
 analyzing, from a subject having depression and currently or previously being treated with a composition, a biological sample to determine the level(s) of one or more biomarkers for depression, wherein the one or more biomarkers are selected from Tables 1, 2, and 3; and
 comparing the level(s) of the one or more biomarkers in the sample to (a) levels of the one or more biomarkers in a previously-taken biological sample from the subject, wherein the previously-taken biological sample was obtained from the subject before being treated with the composition, (b) depression-positive reference levels of the one or more biomarkers, (c) depression-negative reference levels of the one or more biomarkers, (d) depression-progression-positive reference levels of the one or more biomarkers, and/or (e) depression-regression-positive reference levels of the one or more biomarkers.

In yet a further aspect, a method for assessing the efficacy of a composition in treating depression is provided comprising:
 analyzing a first biological sample from a subject to determine the level(s) of one or more biomarkers for depression, the first sample obtained from the subject at a first time point, wherein the one or more biomarkers are selected from Tables 1, 2, and 3;

administering the composition to the subject;

analyzing a second biological sample from the subject to determine the level(s) of the one or more biomarkers, the second sample obtained from the subject at a second time point after administration of the composition; and comparing the level(s) of one or more biomarkers in the first sample to the level(s) of the one or more biomarkers in the second sample in order to assess the efficacy of the composition for treating depression.

In another aspect, a method of assessing the relative efficacy of two or more compositions for treating depression is provided. The method comprises:

analyzing, from a first subject having depression and currently or previously being treated with a first composition, a first biological sample to determine the level(s) of one or more biomarkers for depression, wherein the one or more biomarkers are selected from Tables 1, 2, and 3;

analyzing, from a second subject having depression and currently or previously being treated with a second composition, a second biological sample to determine the level(s) of the one or more biomarkers; and comparing the level(s) of one or more biomarkers in the first sample to the level(s) of the one or more biomarkers in the second sample in order to assess the relative efficacy of the first and second compositions for treating depression.

In yet another aspect, a method for screening a composition for activity in modulating one or more biomarkers of depression is provided comprising:

contacting one or more cells with a composition;

analyzing at least a portion of the one or more cells or a biological sample associated with the cells to determine the level(s) of one or more biomarkers of depression, wherein the one or more biomarkers are selected from Tables 1, 2, and 3; and comparing the level(s) of the one or more biomarkers with predetermined standard levels for the biomarkers to determine whether the composition modulated the level(s) of the one or more biomarkers.

In a further aspect, a method for identifying a potential drug target for depression is provided. The method comprises:

identifying one or more biochemical pathways associated with one or more biomarkers for depression, wherein the one or more biomarkers are selected from Tables 1, 2, and 3; and identifying a protein affecting at least one of the one or more identified biochemical pathways, the protein being a potential drug target for depression.

In another aspect, a method for treating a subject having depression is provided. The method comprises administering to the subject an effective amount of one or more biomarkers selected from Table 1 that are decreased in subjects having depression as compared to subjects not having depression.

DETAILED DESCRIPTION

The present invention relates to biomarkers of depression, methods for diagnosis of depression, methods of determining predisposition to depression, methods of monitoring progression/regression of depression, methods of assessing efficacy of compositions for treating depression, methods of screening compositions for activity in modulating biomarkers of depression, methods of treating depression, as well as other methods based on biomarkers of depression. Prior to describing this invention in further detail, however, the following terms will first be defined.

DEFINITIONS

"Biomarker" means a compound, preferably a metabolite, that is differentially present (i.e., increased or decreased) in a biological sample from a subject or a group of subjects having a first phenotype (e.g., having a disease) as compared to a biological sample from a subject or group of subjects having a second phenotype (e.g., not having the disease). A biomarker may be differentially present at any level, but is generally present at a level that is increased by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, by at least 100%, by at least 110%, by at least 120%, by at least 130%, by at least 140%, by at least 150%, or more; or is generally present at a level that is decreased by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, or by 100% (i.e., absent). A biomarker is preferably differentially present at a level that is statistically significant (i.e., a p-value less than 0.05 as determined using either Welch's T-test or Wilcoxon's rank-sum Test).

The "level" of one or more biomarkers means the absolute or relative amount or concentration of the biomarker in the sample.

"Sample" or "biological sample" means biological material isolated from a subject. The biological sample may contain any biological material suitable for detecting the desired biomarkers, and may comprise cellular and/or non-cellular material from the subject. The sample can be isolated from any suitable biological tissue or fluid such as, for example, blood, blood plasma, urine, or cerebral spinal fluid (CSF).

"Subject" means any animal, but is preferably a mammal, such as, for example, a human, monkey, mouse, or rabbit.

A "reference level" of a biomarker means a level of the biomarker that is indicative of a particular disease state, phenotype, or lack thereof, as well as combinations of disease states, phenotypes, or lack thereof. A "positive" reference level of a biomarker means a level that is indicative of a particular disease state or phenotype. A "negative" reference level of a biomarker means a level that is indicative of a lack of a particular disease state or phenotype. For example, a "depression-positive reference level" of a biomarker means a level of a biomarker that is indicative of a positive diagnosis of depression in a subject, and a "depression-negative reference level" of a biomarker means a level of a biomarker that is indicative of a negative diagnosis of depression in a subject. As another example, a "depression-progression-positive reference level" of a biomarker means a level of a biomarker that is indicative of progression of depression in a subject, and a "depression-regression-positive reference level" of a biomarker means a level of a biomarker that is indicative of regression of depression in a subject. A "reference level" of a biomarker may be an absolute or relative amount or concentration of the biomarker, a presence or absence of the biomarker, a range of amount or concentration of the biomarker, a minimum and/or maximum amount or concentration of the biomarker, a mean amount or concentration of the biomarker, and/or a median amount or concentration of the biomarker; and, in addition, "reference levels" of combinations of biomarkers may also be ratios of absolute or relative amounts or concentrations of two or more biomarkers with respect to each other. Appropriate positive and negative reference levels of biomarkers for a particular disease state, phenotype, or lack thereof may be determined by measuring levels of desired biomarkers in one or more appropriate subjects, and such reference levels may be tailored to specific populations of subjects (e.g., a reference level may be age-matched so that comparisons may be made between biomarker levels in samples from subjects of a certain age and reference levels for a particular disease state, phenotype, or lack thereof in a certain age group). Such reference levels may also be tailored to specific techniques that are used to measure levels of biomarkers in biological samples (e.g., LC-MS, GC-MS, etc.), where the levels of biomarkers may differ based on the specific technique that is used.

"Non-biomarker compound" means a compound that is not differentially present in a biological sample from a subject or a group of subjects having a first phenotype (e.g., having a first disease) as compared to a biological sample from a subject or group of subjects having a second phenotype (e.g., not having the first disease). Such non-biomarker compounds may, however, be biomarkers in a biological sample from a subject or a group of subjects having a third phenotype (e.g., having a second disease) as compared to the first phenotype (e.g., having the first disease) or the second phenotype (e.g., not having the first disease).

"Metabolite", or "small molecule", means organic and inorganic molecules which are present in a cell. The term does not include large macromolecules, such as large proteins (e.g., proteins with molecular weights over 2,000, 3,000, 4,000, 5,000, 6,000, 7,000, 8,000, 9,000, or 10,000), large nucleic acids (e.g., nucleic acids with molecular weights of over 2,000, 3,000, 4,000, 5,000, 6,000, 7,000, 8,000, 9,000, or 10,000), or large polysaccharides (e.g., polysaccharides with a molecular weights of over 2,000, 3,000, 4,000, 5,000, 6,000, 7,000, 8,000, 9,000, or 10,000). The small molecules of the cell are generally found free in solution in the cytoplasm or in other organelles, such as the mitochondria, where they form a pool of intermediates which can be metabolized further or used to generate large molecules, called macromolecules. The term "small molecules" includes signaling molecules and intermediates in the chemical reactions that transform energy derived from food into usable forms. Examples of small molecules include sugars, fatty acids, amino acids, nucleotides, intermediates formed during cellular processes, and other small molecules found within the cell.

"Metabolic profile", or "small molecule profile", means a complete or partial inventory of small molecules within a targeted cell, tissue, organ, organism, or fraction thereof (e.g., cellular compartment). The inventory may include the quantity and/or type of small molecules present. The "small molecule profile" may be determined using a single technique or multiple different techniques.

"Metabolome" means all of the small molecules present in a given organism.

"Depression" refers to clinical depression, also known as major depression or major depressive disorder.

"Psychiatric disorder" refers to depression, mood disorders, anxiety disorders, personality disorders, and other mental disorders as described in the Merck Manual of Diagnosis and Therapy, Section 15 and the Diagnostic and Statistical Manual of Mental Disorders, 4$^{th}$ Edition, (DSM-IV) published by the American Psychiatric Association.

I. Biomarkers

The depression biomarkers described herein were discovered using metabolomic profiling techniques. Such metabolomic profiling techniques are described in more detail in the Examples set forth below as well as in U.S. Pat. No. 7,005,255 and U.S. patent application Ser. Nos. 11/357,732, 10/695,265 (Publication No. 2005/0014132), Ser. No. 11/301,077 (Publication No. 2006/0134676), Ser. No. 11/301,078 (Publication No. 2006/0134677), Ser. No. 11/301,079 (Publication No. 2006/0134678), and Ser. No. 11/405,033, the entire contents of which are hereby incorporated herein by reference.

Generally, metabolic profiles were determined for biological samples from human subjects diagnosed with depression as well as from one or more other groups of human subjects (e.g., healthy control subjects not diagnosed with depression). The metabolic profile for depression was compared to the metabolic profile for biological samples from the one or more other groups of subjects. Those molecules differentially present, including those molecules differentially present at a level that is statistically significant, in the metabolic profile of samples from subjects with depression as compared to another group (e.g., healthy control subjects not diagnosed with depression) were identified as biomarkers to distinguish those groups.

The biomarkers are discussed in more detail herein. The biomarkers that were discovered correspond with the following group(s):

Biomarkers for distinguishing depression vs. control subjects not diagnosed with depression (see Table 1).
Biomarkers for distinguishing depression vs. patients in remission from depression (see Table 2).
Biomarkers for distinguishing remission vs. control subjects not diagnosed with depression (see Table 3).

Although the identities of some of the biomarkers compounds are not known at this time, such identities are not necessary for the identification of the biomarkers in biological samples from subjects, as the "unnamed" compounds have been sufficiently characterized by analytical techniques to allow such identification. The analytical characterization of all such "unnamed" compounds is listed in the Examples. Such "unnamed" biomarkers are designated herein using the nomenclature "Metabolite" followed by a specific metabolite number.

Where the potential identity of a compound is proposed for an "unnamed" metabolite and such identity has not been confirmed, the nomenclature of "possible" (along with the potential compound identity) is indicated along with, in some cases, the "Metabolite" number. Such proposed identity should not be considered as limiting the analytical characterization of the otherwise "unnamed" compounds.

II. Diagnosis of Depression

The identification of biomarkers for depression allows for the diagnosis of (or for aiding in the diagnosis of) depression in subjects presenting one or more symptoms of depression. A method of diagnosing (or aiding in diagnosing) whether a subject has depression comprises (1) analyzing a biological sample from a subject to determine the level(s) of one or more biomarkers of depression in the sample and (2) comparing the level(s) of the one or more biomarkers in the sample to depression-positive and/or depression-negative reference levels of the one or more biomarkers in order to diagnose (or aid in the diagnosis of) whether the subject has depression. The one or more biomarkers that are used are selected from Tables 1, 2 and/or 3 and combinations thereof. When such a method is used to aid in the diagnosis of depression, the results of the method may be used along with other methods (or the results thereof) useful in the clinical determination of whether a subject has depression.

Any suitable method may be used to analyze the biological sample in order to determine the level(s) of the one or more biomarkers in the sample. Suitable methods include chromatography (e.g., HPLC, gas chromatography, liquid chromatography), mass spectrometry (e.g., MS, MS-MS), enzyme-linked immunosorbent assay (ELISA), antibody linkage, other immunochemical techniques, other biochemical techniques, other analytical chemistry techniques, and combinations thereof. Further, the level(s) of the one or more biomarkers may be measured indirectly, for example, by using an assay that measures the level of a compound (or compounds) that correlates with the level of the biomarker(s) that are desired to be measured.

The levels of one or more of the biomarkers of Tables 1, 2 and/or 3 may be determined in the methods of diagnosing and methods of aiding in diagnosing whether a subject has depression. For example, the level(s) of one biomarker, two or more biomarkers, three or more biomarkers, four or more biomarkers, five or more biomarkers, six or more biomarkers, seven or more biomarkers, eight or more biomarkers, nine or more biomarkers, ten or more biomarkers, etc., including a combination of all of the biomarkers in Tables 1, 2 and/or 3 or any fraction thereof, may be determined and used in such methods. Determining levels of combinations of the biomarkers may allow greater sensitivity and specificity in diagnosing depression and aiding in the diagnosis of depression, and may allow better differentiation of depression from other psychiatric disorders (e.g., anxiety disorder, schizophrenia, etc.) that may have similar or overlapping biomarkers to depression (as compared to a subject not having depression). For example, ratios of the levels of certain biomarkers (and non-biomarker compounds) in biological samples may allow greater sensitivity and specificity in diagnosing depression and aiding in the diagnosis of depression, and may allow better differentiation of depression from other psychiatric disorders that may have similar or overlapping biomarkers to depression (as compared to a subject not having a psychiatric disorder).

One or more biomarkers that are specific for diagnosing depression (or aiding in diagnosing depression) in a certain type of sample (e.g., urine sample, CSF sample or blood plasma sample) may also be used. For example, when the biological sample is blood plasma, one or more biomarkers listed in Tables 1, 2, and 3 may be used to diagnose (or aid in diagnosing) whether a subject has depression.

After the level(s) of the one or more biomarkers in the sample are determined, the level(s) are compared to depression-positive and/or depression-negative reference levels to aid in diagnosing or to diagnose whether the subject has depression. Levels of the one or more biomarkers in a sample corresponding to the depression-positive reference levels (e.g., levels that are the same as the reference levels, substantially the same as the reference levels, above and/or below the minimum and/or maximum of the reference levels, and/or within the range of the reference levels) are indicative of a diagnosis of depression in the subject. Levels of the one or more biomarkers in a sample corresponding to the depression-negative reference levels (e.g., levels that are the same as the reference levels, substantially the same as the reference levels, above and/or below the minimum and/or maximum of the reference levels, and/or within the range of the reference levels) are indicative of a diagnosis of no depression in the subject. In addition, levels of the one or more biomarkers that are differentially present (especially at a level that is statistically significant) in the sample as compared to depression-negative reference levels are indicative of a diagnosis of depression in the subject. Levels of the one or more biomarkers that are differentially present (especially at a level that is statistically significant) in the sample as compared to depression-positive reference levels are indicative of a diagnosis of no depression in the subject.

The level(s) of the one or more biomarkers may be compared to depression-positive and/or depression-negative reference levels using various techniques, including a simple comparison (e.g., a manual comparison) of the level(s) of the one or more biomarkers in the biological sample to depression-positive and/or depression-negative reference levels. The level(s) of the one or more biomarkers in the biological sample may also be compared to depression-positive and/or depression-negative reference levels using one or more statistical analyses (e.g., t-test, Welch's T-test, Wilcoxon's rank sum test, random forest).

In addition, the biological samples may be analyzed to determine the level(s) of one or more non-biomarker compounds. The level(s) of such non-biomarker compounds may also allow differentiation of depression from other psychiatric disorders that may have similar or overlapping biomarkers to depression (as compared to a subject not having a psychiatric disorder). For example, a known non-biomarker compound present in biological samples of subjects having depression and subjects not having depression could be monitored to verify a diagnosis of depression as compared to a diagnosis of another psychiatric disorder when biological samples from subjects having the psychiatric disorder do not have the non-biomarker compound.

III. Methods of Determining Predisposition to Depression

The identification of biomarkers for depression also allows for the determination of whether a subject having no symptoms of depression is predisposed to developing depression. A method of determining whether a subject having no symptoms of depression is predisposed to developing depression comprises (1) analyzing a biological sample from a subject to determine the level(s) of one or more biomarkers listed in Tables 1, 2, and/or 3 in the sample and (2) comparing the level(s) of the one or more biomarkers in the sample to depression-positive and/or depression-negative reference levels of the one or more biomarkers in order to determine whether the subject is predisposed to developing depression. The results of the method may be used along with other methods (or the results thereof) useful in the clinical determination of whether a subject is predisposed to developing depression.

As described above in connection with methods of diagnosing (or aiding in the diagnosis of) depression, any suitable method may be used to analyze the biological sample in order to determine the level(s) of the one or more biomarkers in the sample.

As with the methods of diagnosing (or aiding in the diagnosis of) depression described above, the level(s) of one biomarker, two or more biomarkers, three or more biomarkers, four or more biomarkers, five or more biomarkers, six or more biomarkers, seven or more biomarkers, eight or more biomarkers, nine or more biomarkers, ten or more biomarkers, etc., including a combination of all of the biomarkers in Tables 1, 2 and/or 3 or any fraction thereof, may be determined and used in methods of determining whether a subject having no symptoms of depression is predisposed to developing depression.

After the level(s) of the one or more biomarkers in the sample are determined, the level(s) are compared to depression-positive and/or depression-negative reference levels in order to predict whether the subject is predisposed to developing depression. Levels of the one or more biomarkers in a sample corresponding to the depression-positive reference levels (e.g., levels that are the same as the reference levels, substantially the same as the reference levels, above and/or below the minimum and/or maximum of the reference levels, and/or within the range of the reference levels) are indicative of the subject being predisposed to developing depression. Levels of the one or more biomarkers in a sample corresponding to the depression-negative reference levels (e.g., levels that are the same as the reference levels, substantially the same as the reference levels, above and/or below the minimum and/or maximum of the reference levels, and/or within the range of the reference levels) are indicative of the subject not being predisposed to developing depression. In addition, levels of the one or more biomarkers that are differentially present (especially at a level that is statistically significant) in the sample as compared to depression-negative reference levels are indicative of the subject being predisposed to developing depression. Levels of the one or more biomarkers that are differentially present (especially at a level that is statistically significant) in the sample as compared to depression-positive reference levels are indicative of the subject not being predisposed to developing depression.

Furthermore, it may also be possible to determine reference levels specific to assessing whether or not a subject that does not have depression is predisposed to developing depression. For example, it may be possible to determine reference levels of the biomarkers for assessing different degrees of risk (e.g., low, medium, high) in a subject for developing depression. Such reference levels could be used for comparison to the levels of the one or more biomarkers in a biological sample from a subject.

As with the methods described above, the level(s) of the one or more biomarkers may be compared to depression-positive and/or depression-negative reference levels using various techniques, including a simple comparison, one or more statistical analyses, and combinations thereof.

As with the methods of diagnosing (or aiding in diagnosing) whether a subject has depression, the methods of determining whether a subject having no symptoms of depression is predisposed to developing depression may further comprise analyzing the biological sample to determine the level(s) of one or more non-biomarker compounds.

IV. Methods of Monitoring Progression/Regression of Depression

The identification of biomarkers for depression also allows for monitoring progression/regression of depression in a subject. A method of monitoring the progression/regression of depression in a subject comprises (1) analyzing a first biological sample from a subject to determine the level(s) of one or more biomarkers for depression selected from Tables 1, 2, and/or 3, the first sample obtained from the subject at a first time point, (2) analyzing a second biological sample from a subject to determine the level(s) of the one or more biomarkers, the second sample obtained from the subject at a second time point, and (3) comparing the level(s) of one or more biomarkers in the first sample to the level(s) of the one or more biomarkers in the second sample in order to monitor the progression/regression of depression in the subject. The results of the method are indicative of the course of depression (i.e., progression or regression, if any change) in the subject.

The change (if any) in the level(s) of the one or more biomarkers over time may be indicative of progression or regression of depression in the subject. In order to characterize the course of depression in the subject, the level(s) of the one or more biomarkers in the first sample, the level(s) of the one or more biomarkers in the second sample, and/or the results of the comparison of the levels of the biomarkers in the first and second samples may be compared to depression-positive and/or depression-negative reference levels of the one or more biomarkers. If the comparisons indicate that the level(s) of the one or more biomarkers are increasing or decreasing over time (e.g., in the second sample as compared to the first sample) to become more similar to the depression-positive reference levels (or less similar to the depression-negative reference levels), then the results are indicative of depression progression. If the comparisons indicate that the level(s) of the one or more biomarkers are increasing or decreasing over time to become more similar to the depression-negative reference levels (or less similar to the depression-positive reference levels), then the results are indicative of depression regression.

The course of depression in the subject may also be characterized by comparing the level(s) of the one or more biomarkers in the first sample, the level(s) of the one or more biomarkers in the second sample, and/or the results of the comparison of the levels of the biomarkers in the first and second samples to depression-progression-positive and/or depression-regression-positive reference levels (e.g., Example 1 and Table 2 below describe biomarkers for distinguishing subjects with depression from subjects in remission from depression indicating whether certain biomarkers increase or decrease as depression remits; such trends and/or levels of biomarkers in subjects in remission from depression versus subjects having depression are one example of depression-remission-positive reference levels). If the comparisons indicate that the level(s) of the one or more biomarkers are increasing or decreasing over time (e.g., in the second sample as compared to the first sample) to become more similar to the depression-progression-positive reference levels (or less similar to the depression-regression-positive reference levels), then the results are indicative of depression progression. If the comparisons indicate that the level(s) of the one or more biomarkers are increasing or decreasing over time to become more similar to the depression-regression-positive reference levels (or less similar to the depression-progression-positive reference levels), then the results are indicative of depression regression.

As with the other methods described herein, the comparisons made in the methods of monitoring progression/regression of depression in a subject may be carried out using various techniques, including simple comparisons, one or more statistical analyses, and combinations thereof.

The results of the method may be used along with other methods (or the results thereof) useful in the clinical monitoring of progression/regression of depression in a subject.

As described above in connection with methods of diagnosing (or aiding in the diagnosis of) depression, any suitable method may be used to analyze the biological samples in order to determine the level(s) of the one or more biomarkers in the samples. In addition, the level(s) one or more biomarkers, including a combination of all of the biomarkers in. Tables 1, 2, and/or 3 or any fraction thereof, may be determined and used in methods of monitoring progression/regression of depression in a subject.

Such methods could be conducted to monitor the course of depression in subjects having depression or could be used in subjects not having depression (e.g., subjects suspected of being predisposed to developing depression) in order to monitor levels of predisposition to depression.

V. Methods of Assessing Efficacy of Compositions for Treating Depression

The identification of biomarkers for depression also allows for assessment of the efficacy of a composition for treating depression as well as the assessment of the relative efficacy of two or more compositions for treating depression. Such assessments may be used, for example, in efficacy studies as well as in lead selection of compositions for treating depression.

A method of assessing the efficacy of a composition for treating depression comprises (1) analyzing, from a subject having depression and currently or previously being treated with a composition, a biological sample to determine the level(s) of one or more biomarkers selected from Tables 1, 2, and/or 3, and (2) comparing the level(s) of the one or more biomarkers in the sample (or group of samples) to (a) level(s) of the one or more biomarkers in a previously-taken biological sample (or group of samples) from the subject (or group of subjects), wherein the previously-taken biological sample (or group of samples) was obtained from the subject (or group of subjects) before being treated with the composition, (b) depression-positive reference levels of the one or more biomarkers, (c) depression-negative reference levels of the one or more biomarkers, and/or (d) depression-progression-positive reference levels of the one or more biomarkers, and/or (e) depression-regression-positive reference levels of the one or more biomarkers. The results of the comparison are indicative of the efficacy of the composition for treating depression.

Thus, in order to characterize the efficacy of the composition for treating depression, the level(s) of the one or more biomarkers in the biological sample are compared to (1) depression-positive reference levels, (2) depression-negative reference levels, and/or (3) depression-progression-positive reference levels, (4) depression-regression-positive reference levels, and/or (5) previous levels of the one or more biomarkers in the subject (or group of subjects) before treatment with the composition.

When comparing the level(s) of the one or more biomarkers in the biological sample (from a subject or group of subjects having depression and currently or previously being treated with a composition) to depression-positive reference levels, depression-negative reference levels, depression-progression-positive reference levels, and/or depression-regression-positive reference levels, level(s) in the sample corresponding to the depression-negative reference levels or depression-regression-positive reference levels (e.g., levels that are the same as the reference levels, substantially the same as the reference levels, above and/or below the minimum and/or maximum of the reference levels, and/or within the range of the reference levels) are indicative of the composition having efficacy for treating depression. Levels of the one or more biomarkers in the sample corresponding to the depression-positive reference levels or depression-progression-positive reference levels (e.g., levels that are the same as the reference levels, substantially the same as the reference levels, above and/or below the minimum and/or maximum of the reference levels, and/or within the range of the reference levels) are indicative of the composition not having efficacy for treating depression. The comparisons may also indicate degrees of efficacy for treating depression based on the level(s) of the one or more biomarkers.

When the level(s) of the one or more biomarkers in the biological sample(s) (from a subject or group of subjects having depression and currently or previously being treated with a composition) are compared to level(s) of the one or more biomarkers in a previously-taken biological sample(s) from the subject (or group of subjects) before treatment with the composition, any changes in the level(s) of the one or more biomarkers are indicative of the efficacy of the composition for treating depression. That is, if the comparisons indicate that the level(s) of the one or more biomarkers have increased or decreased after treatment with the composition to become more similar to the depression-negative or depression-regression-positive reference levels (or less similar to the depression-positive or depression-progression-positive reference levels), then the results are indicative of the composition having efficacy for treating depression. If the comparisons indicate that the level(s) of the one or more biomarkers have not increased or decreased after treatment with the composition to become more similar to the depression-negative or depression-regression-positive reference levels (or less similar to the depression-positive or depression-progression-positive reference levels), then the results are indicative of the composition not having efficacy for treating depression. The comparisons may also indicate degrees of efficacy for treating depression based on the amount of changes observed in the level(s) of the one or more biomarkers after treatment. In order to help characterize such a comparison, the changes in the level(s) of the one or more biomarkers, the level(s) of the one or more biomarkers before treatment, and/or the level(s) of the one or more biomarkers in the subject currently or previously being treated with the composition may be compared to depression-positive, depression-negative, depression-regression-positive, and/or depression-progression-positive reference levels of the one or more biomarkers.

Another method for assessing the efficacy of a composition in treating depression comprises (1) analyzing a first biological sample (or group of samples) from a subject (or group of subjects) to determine the level(s) of one or more biomarkers selected from Tables 1, 2, and/or 3, the first sample obtained from the subject at a first time point, (2) administering the composition to the subject, (3) analyzing a second biological sample from a subject to determine the level(s) of the one or more biomarkers, the second sample obtained from the subject at a second time point after administration of the composition, and (4) comparing the level(s) of one or more biomarkers in the first sample to the level(s) of the one or more biomarkers in the second sample in order to assess the efficacy of the composition for treating depression. As indicated above, if the comparison of the samples indicates that the level(s) of the one or more biomarkers have increased or decreased after administration of the composition to become more similar to the depression-negative or depression-regression-positive reference levels (or less similar to the depression-positive or depression-progression-positive reference levels), then the results are indicative of the composition having efficacy for treating depression. If the comparison indicates that the level(s) of the one or more biomarkers have not increased or decreased after administration of the composition to become more similar to the depression-negative or depression-regression-positive reference levels (or less similar to the depression-positive or depression-progression-positive reference levels), then the results are indicative of the composition not having efficacy for treating depression. The comparison may also indicate a degree of efficacy for treating depression based on the amount of changes observed in the level(s) of the one or more biomarkers after administration of the composition. In order to help characterize such a comparison, the changes in the level(s) of the one or more biomarkers, the level(s) of the one or more biomarkers before administration of the composition, and/or the level(s) of the one or more biomarkers after administration of the composition may be compared to depression-positive, depression-negative, depression-regression-positive, and/or depression-progression-positive reference levels of the one or more biomarkers of the two compositions.

A method of assessing the relative efficacy of two or more compositions for treating depression comprises (1) analyzing, from a first subject having depression and currently or previously being treated with a first composition, a first biological sample to determine the level(s) of one or more biomarkers selected from Tables 1, 2, and/or 3 (2) analyzing, from a second subject having depression and currently or previously being treated with a second composition, a second biological sample to determine the level(s) of the one or more biomarkers, and (3) comparing the level(s) of one or more biomarkers in the first sample to the level(s) of the one or more biomarkers in the second sample in order to assess the relative efficacy of the first and second compositions for treating depression. The results are indicative of the relative efficacy of the two compositions, and the results (or the levels of the one or more biomarkers in the first sample and/or the level(s) of the one or more biomarkers in the second sample) may be compared to depression-positive, depression-negative, depression-regression-positive, and/or depression-progression-positive reference levels to aid in characterizing the relative efficacy.

Each of the methods of assessing efficacy may be conducted on one or more subjects or one or more groups of subjects (e.g., a first group being treated with a first composition and a second group being treated with a second composition).

As with the other methods described herein, the comparisons made in the methods of assessing efficacy (or relative efficacy) of compositions for treating depression may be carried out using various techniques, including simple comparisons, one or more statistical analyses, and combinations thereof. Any suitable method may be used to analyze the biological samples in order to determine the level(s) of the one or more biomarkers in the samples. In addition, the level(s) of one or more biomarkers, including a combination of all of the biomarkers in Tables 1, 2, and/or 3 or any fraction thereof, may be determined and used in methods of assessing efficacy (or relative efficacy) of compositions for treating depression.

Finally, the methods of assessing efficacy (or relative efficacy) of one or more compositions for treating depression may further comprise analyzing the biological sample to determine the level(s) of one or more non-biomarker compounds. The non-biomarker compounds may then be compared to reference levels of non-biomarker compounds for subjects having (or not having) depression.

VI. Methods of Screening a Composition for Activity in Modulating Biomarkers Associated with Depression The identification of biomarkers for depression also allows for the screening of compositions for activity in modulating biomarkers associated with depression, which may be useful in treating depression. Methods of screening compositions useful for treatment of depression comprise assaying test compositions for activity in modulating the levels of one or more biomarkers in Tables 1, 2 and/or 3. Such screening assays may be conducted in vitro and/or in vivo, and may be in any form known in the art useful for assaying modulation of such biomarkers in the presence of a test composition such as, for example, cell culture assays, organ culture assays, and in vivo assays (e.g., assays involving animal models).

In one embodiment, a method for screening a composition for activity in modulating one or more biomarkers of depression comprises (1) contacting one or more cells with a composition, (2) analyzing at least a portion of the one or more cells or a biological sample associated with the cells to determine the level(s) of one or more biomarkers of depression selected from. Tables 1, 2, and/or 3; and (3) comparing the level(s) of the one or more biomarkers with predetermined standard levels for the one or more biomarkers to determine whether the composition modulated the level(s) of the one or more biomarkers. As discussed above, the cells may be contacted with the composition in vitro and/or in vivo. The predetermined standard levels for the one or more biomarkers may be the levels of the one or more biomarkers in the one or more cells in the absence of the composition. The predetermined standard levels for the one or more biomarkers may also be the level(s) of the one or more biomarkers in control cells not contacted with the composition.

In addition, the methods may further comprise analyzing at least a portion of the one or more cells or a biological sample associated with the cells to determine the level(s) of one or more non-biomarker compounds of depression. The levels of the non-biomarker compounds may then be compared to predetermined standard levels of the one or more non-biomarker compounds.

Any suitable method may be used to analyze at least a portion of the one or more cells or a biological sample associated with the cells in order to determine the level(s) of the one or more biomarkers (or levels of non-biomarker compounds). Suitable methods include chromatography (e.g., HPLC, gas chromatograph, liquid chromatography), mass spectrometry (e.g., MS, MS-MS), ELISA, antibody linkage, other immunochemical techniques, and combinations thereof. Further, the level(s) of the one or more biomarkers (or levels of non-biomarker compounds) may be measured indirectly, for example, by using an assay that measures the level of a compound (or compounds) that correlates with the level of the biomarker(s) (or non-biomarker compounds) that are desired to be measured.

VII. Method of Identifying Potential Drug Targets

The identification of biomarkers for depression also allows for the identification of potential drug targets for depression. A method for identifying a potential drug target for depression comprises (1) identifying one or more biochemical pathways associated with one or more biomarkers for depression selected from Tables 1, 2 and/or 3 and (2) identifying a protein (e.g., an enzyme) affecting at least one of the one or more identified biochemical pathways, the protein being a potential drug target for depression.

Another method for identifying a potential drug target for depression comprises (1) identifying one or more biochemical pathways associated with one or more biomarkers for depression selected from Tables 1, 2 and/or 3 and one or more non-biomarker compounds of depression and (2) identifying a protein affecting at least one of the one or more identified biochemical pathways, the protein being a potential drug target for depression.

One or more biochemical pathways (e.g., biosynthetic and/or metabolic (catabolic) pathway) are identified that are associated with one or more biomarkers (or non-biomarker compounds). After the biochemical pathways are identified, one or more proteins affecting at least one of the pathways are identified. Preferably, those proteins affecting more than one of the pathways are identified.

A build-up of one metabolite (e.g., a pathway intermediate) may indicate the presence of a 'block' downstream of the metabolite and the block may result in a low/absent level of a downstream metabolite (e.g. product of a biosynthetic pathway). In a similar manner, the absence of a metabolite could indicate the presence of a 'block' in the pathway upstream of the metabolite resulting from inactive or non-functional enzyme(s) or from unavailability of biochemical intermediates that are required substrates to produce the product. Alternatively, an increase in the level of a metabolite could indicate a genetic mutation that produces an aberrant protein which results in the over-production and/or accumulation of a metabolite which then leads to an alteration of other related biochemical pathways and result in dysregulation of the normal flux through the pathway; further, the build-up of the biochemical intermediate metabolite may be toxic or may compromise the production of a necessary intermediate for a related pathway. It is possible that the relationship between pathways is currently unknown and this data could reveal such a relationship.

For example, several fatty acids, small organic acids and GABA were reduced in the depressed patients compared to the controls. These same compounds were higher in patients in remission compared to depressed patients. These observations suggest that depression may be associated with alterations in the metabolism of lipids and neurotransmitters, and that treatment with antidepressants adjusts aberrant pathways in disease so that the patients in remission have a metabolic profile more similar to healthy controls. The pathways leading to the production of any decreased biomarker would provide a number of potential targets for drug discovery.

The proteins identified as potential drug targets may then be used to identify compositions that may be potential candidates for treating depression, including compositions for gene therapy.

VIII. Methods of Treating Depression

The identification of biomarkers for depression also allows for the treatment of depression. For example, in order to treat a subject having depression, an effective amount of one or more depression biomarkers that are lowered in depression as compared to a healthy subject not having depression may be administered to the subject. The biomarkers that may be administered may comprise one or more of the biomarkers in Tables 1, 2 and/or 3 that are decreased in subjects having depression. In some embodiments, the biomarkers that are administered are one or more biomarkers listed in Tables 1, 2 and/or 3 that are decreased in depression and that have a p-value less than 0.10 or those that have a p-value less than 0.05. In other embodiments, the biomarkers that are administered are one or biomarkers listed in Tables 1, 2 and/or 3 that are decreased in depression by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, or by 100% (i.e., absent).

IX. Methods of Using the Depression Biomarkers for Other Types of Depression

It is believed that some of the biomarkers for major depression described herein may also be biomarkers for other types of depression, including, for example, melancholic depression, atypical depression, bipolar depression, psychotic bipolar, cyclothymic disorder, dysthymia, mood disorder, substance-induced mood disorder, seasonal affective disorder (SAD), post-partum depression, and premenstrual dysphoric disorder. Therefore, it is believed that at least some of the depression biomarkers may be used in the methods described herein for other types of depression. That is, the methods described herein with respect to depression may also be used for diagnosing (or aiding in the diagnosis of) any type of depression, methods of monitoring progression/regression of any type of depression, methods of assessing efficacy of compositions for treating any type of depression, methods of screening a composition for activity in modulating biomarkers associated with any type of depression, methods of identifying potential drug targets for any type of depression, and methods of treating any type of depression. Such methods could be conducted as described herein with respect to depression.

X. Methods of Using the Depression Biomarkers for Other Psychiatric Disorders

It is believed that some of the biomarkers for major depression described herein may also be biomarkers for psychiatric disorders in general. Therefore, it is believed that at least some of the depression biomarkers may be used in the methods described herein for psychiatric disorders in general. That is, the methods described herein with respect to depression may also be used for diagnosing (or aiding in the diagnosis of) a psychiatric disorder, methods of monitoring progression/regression of a psychiatric disorder, methods of assessing efficacy of compositions for treating a psychiatric disorder, methods of screening a composition for activity in modulating biomarkers associated with a psychiatric disorder, methods of identifying potential drug targets for psychiatric disorder, and methods of treating a psychiatric disorder. Such methods could be conducted as described herein with respect to depression.

XI. Other Methods

Other methods of using the biomarkers discussed herein are also contemplated. For example, the methods described in U.S. Pat. No. 7,005,255 and U.S. patent application Ser. No. 10/695,265 may be conducted using a small molecule profile comprising one or more of the biomarkers disclosed herein.

In any of the methods listed herein, the biomarkers that are used may be selected from those biomarkers in Tables 1, 2 and/or 3 having p-values of less than 0.10 or those biomarkers in Tables 1, 2 and/or 3 having p-values of less than 0.05. The biomarkers that are used in any of the methods described herein may also be selected from those biomarkers in Tables 1, 2 and/or 3 that are decreased in depression (as compared to the control or remission) or that are decreased in remission (as compared to control or depression) by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, or by 100% (i.e., absent); and/or those biomarkers in Tables 1, 2 and/or 3 that are increased in depression (as compared to the control or remission) or that are increased in remission (as compared to the control or depression) by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, by at least 100%, by at least 110%, by at least 120%, by at least 130%, by at least 140%, by at least 150%, or more.

EXAMPLES

The invention will be further explained by the following illustrative examples that are intended to be non-limiting.

I. General Methods

A. Identification of Metabolic Profiles for Depression

Each sample was analyzed to determine the concentration of several hundred metabolites. Analytical techniques such as GC-MS (gas chromatography-mass spectrometry) and LC-MS (liquid chromatography-mass spectrometry) were used to analyze the metabolites. Multiple aliquots were simultaneously, and in parallel, analyzed, and, after appropriate quality control (QC), the information derived from each analysis was recombined. Every sample was characterized according to several thousand characteristics, which ultimately amount to several hundred chemical species. The techniques used were able to identify novel and chemically unnamed compounds.

B. Statistical Analysis

The data was analyzed using T-tests to identify molecules (either known, named metabolites or unnamed metabolites) present at differential levels in a definable population or subpopulation (e.g., biomarkers for depression biological samples compared to control biological samples or compared to patients in remission from depression) useful for distinguishing between the definable populations (e.g., depression and control, depression and remission, remission and control). Other molecules (either known, named metabolites or unnamed metabolites) in the definable population or subpopulation were also identified.

C. Biomarker Identification

Various peaks identified in the analyses (e.g. GC-MS, LC-MS, MS-MS), including those identified as statistically significant, were subjected to a mass spectrometry based chemical identification process.

Example 1

Biomarkers were discovered by (1) analyzing blood samples drawn from different groups of human subjects to determine the levels of metabolites in the samples and then (2) statistically analyzing the results to determine those metabolites that were differentially present in the two groups.

The plasma samples used for the analysis were from 9 currently depressed subjects, 11 subjects in remission from depression, and 10 control subjects never diagnosed with depression. After the levels of metabolites were determined, the data was analyzed using univariate T-tests (i.e., Welch's T-test).

Given the small sample size and improvements to the platform used for analysis, the samples were re-analyzed. In the second analysis the samples were analyzed using both the GC-MS and LC-MS platforms. The trends for the compounds that were initially identified remained the same (e.g. increased or decreased as observed in the first analysis). In addition, more compounds were identified in the second analysis. The biomarker compounds are listed in Tables 1, 2 and 3 below. The correlation of data between the normalized data in set one and the second run is shown in Table 4.

T-tests were used to determine differences in the mean levels of metabolites between two populations (i.e., Depression vs. Control, Remission vs. Control, Depression vs. Remission).

Biomarkers:

As listed below in Table 1, biomarkers were discovered that were differentially present between samples from depression subjects and Control subjects not diagnosed with depression. Table 2 lists biomarkers that were discovered that were differentially present between samples from depression subjects and subjects in remission from depression. Table 3 lists biomarkers that were discovered that were differentially present between samples from subjects in remission from depression and Control subjects not diagnosed with depression.

Tables 1-3 include, for each listed biomarker, the p-value determined in the statistical analysis of the data concerning the biomarkers and an indication of the percentage difference in the depression mean level as compared to the control mean level (Table 1), the depression mean level as compared to the remission mean level (Table 2), and the remission mean level as compared to the control mean level (Table 3). The term "Isobar" as used in the tables indicates the compounds that could not be distinguished from each other on the analytical platform used in the analysis (i.e., the compounds in an isobar elute at nearly the same time and have similar (and sometimes exactly the same) quant ions, and thus cannot be distinguished). Library indicates the chemical library that was used to identify the compounds. The numbers 9 and 50 refer to the GC library and the number 61 refers to the LC library.

TABLE 1

| Depression vs. Control | | | |
|---|---|---|---|
| Compound | Library | p-value | % Change in Depression |
| Metabolite-420 | 9 | 0.0015 | −71% |
| Metabolite-760 | 9 | 0.0028 | −56% |
| Metabolite-568 | 9 | 0.003 | −69% |
| glycerate | 9 | 0.0034 | −70% |
| carnitine | 61 | 0.0066 | −25% |
| Metabolite-279 | 9 | 0.0072 | −85% |
| inositol | 9 | 0.0079 | −65% |
| glucarate | 9 | 0.0101 | −65% |
| 4-aminobutanoic acid | 9 | 0.0109 | −91% |
| Metabolite-3052 | 61 | 0.0124 | 89% |
| citric acid | 9 | 0.0133 | −39% |
| Metabolite-511 | 9 | 0.014 | −26% |
| tetronic acid | 9 | 0.0146 | −61% |
| Metabolite-2812 | 61 | 0.017 | 46% |
| N-N-dimethylarginine | 61 | 0.0184 | −31% |
| Metabolite-763 | 9 | 0.0188 | −66% |
| Metabolite-263 | 9 | 0.0198 | −55% |
| Metabolite-385 | 9 | 0.0213 | −63% |
| 9,12-octadecadienoic acid z-z | 9 | 0.0215 | −148% |
| glycerol | 9 | 0.0216 | −51% |
| alpha-Hydroxyisobutyric acid tms- | 9 | 0.0232 | −52% |
| N-formyl-L-methionine | 61 | 0.0265 | −42% |
| Metabolite-3405 | 61 | 0.0267 | 37% |
| Metabolite-570 | 9 | 0.0268 | −61% |
| Metabolite-1974 | 61 | 0.0279 | −31% |
| Metabolite-480 | 9 | 0.0295 | −94% |
| 5-oxoproline | 9 | 0.031 | −78% |
| Metabolite-4515 | 50 | 0.0323 | −85% |
| Metabolite-223 | 9 | 0.0326 | −52% |
| Metabolite-3065 | 50 | 0.0329 | 34% |
| Metabolite-3994 | 61 | 0.0329 | 43% |
| Metabolite-4359 | 61 | 0.034 | −43% |
| Metabolite-941 | 9 | 0.0358 | −96% |
| Metabolite-3807 | 61 | 0.0361 | −21% |
| glycerate | 61 | 0.0376 | −43% |
| hydroorotate | 9 | 0.0383 | −19% |
| 3-phospho-d-glycerate | 61 | 0.0387 | −33% |
| Metabolite-704 | 9 | 0.0408 | −46% |
| Metabolite-386 | 9 | 0.0415 | −80% |
| 3-phospho-l-serine | 9 | 0.0416 | −61% |
| Metabolite-3980 | 61 | 0.0416 | −36% |
| Metabolite-1114 | 61 | 0.0422 | −31% |
| Metabolite-2548 | 61 | 0.0427 | 36% |
| Metabolite-2279 | 61 | 0.0431 | −31% |
| Metabolite-3709 | 61 | 0.0442 | −55% |
| oxitryptan | 61 | 0.0458 | −34% |
| Metabolite-709 | 9 | 0.0474 | −69% |
| mercaptopyruvate | 61 | 0.0483 | −23% |
| Metabolite-4498 | 50 | 0.0485 | −36% |
| oleic acid | 9 | 0.0495 | −123% |
| Metabolite-995 | 9 | 0.053 | −159% |
| octadecanoic acid | 9 | 0.053 | −85% |
| Metabolite-4233 | 61 | 0.0536 | −30% |
| Metabolite-4161 | 61 | 0.0546 | −44% |
| Metabolite-2027 | 61 | 0.0559 | 26% |
| Metabolite-1465 | 61 | 0.0569 | −24% |
| Metabolite-2249 | 61 | 0.0604 | −32% |
| Metabolite-3653 | 61 | 0.0613 | −57% |
| palmitate | 9 | 0.0616 | −108% |
| Metabolite-3810 | 61 | 0.0619 | −59% |
| Metabolite-2139 | 61 | 0.0631 | −24% |
| Metabolite-2285 | 61 | 0.064 | −33% |

TABLE 1-continued

Depression vs. Control

| Compound | Library | p-value | % Change in Depression |
|---|---|---|---|
| Metabolite-1817 | 61 | 0.0665 | 24% |
| Metabolite-3772 | 61 | 0.0666 | −28% |
| DL-homocysteine | 61 | 0.068 | 28% |
| Metabolite-3218 | 61 | 0.0687 | −37% |
| Isobar-4-includes-Gluconic acid-arabinose-D-ribose-L-xylose-D-lyxose | 61 | 0.072 | −27% |
| Metabolite-404 | 9 | 0.0728 | −80% |
| Metabolite-421 | 9 | 0.0734 | −62% |
| Metabolite-2507 | 61 | 0.075 | −74% |
| Metabolite-221 | 9 | 0.0759 | −206% |
| Metabolite-381 | 9 | 0.0766 | −54% |
| Metabolite-441 | 9 | 0.0787 | −53% |
| Metabolite-462 | 9 | 0.0788 | −55% |
| Metabolite-2781 | 61 | 0.0793 | −38% |
| Metabolite-388 | 9 | 0.0807 | −55% |
| Metabolite-595 | 9 | 0.0824 | −55% |
| Metabolite-4446 | 61 | 0.083 | 63% |
| Metabolite-653 | 9 | 0.0847 | −57% |
| Metabolite-1333 | 61 | 0.085 | −39% |
| Metabolite-651 | 9 | 0.0851 | −52% |
| Metabolite-1573 | 61 | 0.0862 | −38% |
| Metabolite-725 | 9 | 0.0866 | −50% |
| Metabolite-4428 | 61 | 0.0869 | −29% |
| Metabolite-656 | 9 | 0.0882 | 136% |
| palmitoleic acid | 9 | 0.0886 | −121% |
| guanidineacetic acid | 61 | 0.0893 | −39% |
| Metabolite-3578 | 61 | 0.0894 | −27% |
| Metabolite-442 | 9 | 0.09 | −53% |
| possible n-Butylamine | 9 | 0.0901 | −53% |
| Metabolite-501 | 9 | 0.0905 | −51% |
| Metabolite-2185 | 61 | 0.0912 | −33% |
| Metabolite-1829 | 61 | 0.0931 | −25% |
| Metabolite-382 | 9 | 0.0941 | −48% |
| 2-aminobutanoic acid | 9 | 0.0963 | −49% |
| Metabolite-3245 | 61 | 0.0969 | −46% |
| Metabolite-3085 | 50 | 0.0982 | −33% |
| Metabolite-4148 | 50 | 0.0987 | 18% |
| Metabolite-1245 | 61 | 0.0993 | 52% |
| Metabolite-2563 | 61 | 0.0996 | −32% |
| Metabolite-3708 | 61 | 0.0998 | −56% |
| Metabolite-770 | 9 | 0.1 | −16% |
| alpha-methyl-L-beta-3-4-dihydroxyphenylalanine | 50 | 0.1057 | 25% |
| tetradecanoic acid | 9 | 0.1123 | −118% |
| phenylalanine | 9 | 0.1135 | −16% |
| melibiose | 50 | 0.1136 | 68% |
| 3-nitro-L-tyrosine | 50 | 0.1218 | 24% |
| 2-amino-heptanedioic acid | 9 | 0.123 | −48% |
| Isobar-2-includes-3-amino-isobutyrate-2-amino-butyrate-4-aminobutanoic acid-dimethylglycine-choline- | 61 | 0.1248 | −25% |
| cytosine | 61 | 0.1295 | 24% |
| phosphoenolpyruvate | 61 | 0.1319 | −21% |
| histamine | 61 | 0.1379 | 23% |
| phenylalanine | 61 | 0.1392 | −10% |
| chorismate | 61 | 0.1452 | 37% |
| beta-hydroxypyruvic acid | 61 | 0.1551 | 36% |
| threonine | 9 | 0.1556 | −18% |
| glycerol | 50 | 0.1563 | −21% |
| alanine | 9 | 0.1564 | −25% |
| D-alanyl-D-alanine | 61 | 0.1578 | −28% |
| urea | 9 | 0.1627 | −42% |
| cholesterol | 9 | 0.1637 | −24% |
| DOPA | 50 | 0.164 | −31% |
| alpha-tocopherol | 9 | 0.1641 | −62% |
| alpha-aminoadipic acid | 9 | 0.1657 | −37% |
| proline | 9 | 0.1768 | −29% |
| glyceric acid | 50 | 0.1795 | −23% |
| decanoic acid | 9 | 0.1823 | −34% |
| tartarate | 9 | 0.1829 | −35% |
| pentanedioic acid | 9 | 0.1848 | −50% |
| inosine | 9 | 0.1852 | −21% |
| ethylmalonic acid | 61 | 0.1858 | 20% |
| L-alpha-glycerophosphorylcholine | 61 | 0.1905 | 29% |
| tryptophan | 9 | 0.1957 | −78% |
| 5-oxoproline | 50 | 0.1967 | −26% |
| trans-4-hydroxyproline | 50 | 0.2066 | −22% |
| heptanedioic acid | 61 | 0.2068 | −25% |
| arabinose | 50 | 0.2077 | −26% |
| 3-hydroxybutanoic acid | 9 | 0.2084 | −69% |
| Isobar-9-includes-sucrose-beta-D-lactose-D-trehalose-D-cellobiose-D-Maltose-palatinose-melibiose-alpha-D-lactose | 61 | 0.2086 | 26% |
| urea | 50 | 0.2142 | −22% |
| riboflavine | 61 | 0.2206 | 44% |
| 9-12-octadecadienoic acid-z-z- | 50 | 0.2345 | −28% |
| tyrosine | 9 | 0.2362 | −26% |
| 1-7-dihydro-6h-purin-6-one | 61 | 0.2394 | −40% |
| selenocystine | 61 | 0.2416 | 27% |
| Isobar 59: N-6-trimethyl-l-lysine, homoarginine | 61 | 0.2432 | −32% |
| orotidine-5-phosphate | 61 | 0.2543 | 25% |
| taurine | 61 | 0.2611 | 39% |
| alpha-tocopherol | 50 | 0.2654 | −37% |
| histidine | 50 | 0.2682 | 17% |
| catechol | 61 | 0.2728 | −51% |
| leucine | 9 | 0.2785 | −14% |
| picolinic acid | 61 | 0.2812 | 16% |
| octopamine | 50 | 0.2858 | 14% |
| glycine | 50 | 0.286 | 24% |
| tetradecanoic acid | 50 | 0.2893 | −26% |
| Carnosine | 61 | 0.2924 | −19% |
| uric acid | 9 | 0.2951 | −102% |
| arginino-succinate | 61 | 0.3004 | 15% |
| guanosine-5-diphosphate | 61 | 0.3067 | −18% |
| methyl-indole-3-acetate | 61 | 0.3077 | 15% |
| biliverdin | 61 | 0.3118 | 22% |
| serine | 9 | 0.3119 | −15% |
| lactate | 50 | 0.317 | −12% |
| gluconic acid | 50 | 0.317 | −21% |
| 3-amino-isobutyrate | 50 | 0.3176 | 16% |
| octadecanoic acid | 50 | 0.3251 | −13% |
| pyridoxamine-phosphate | 61 | 0.3262 | −29% |
| malonic acid | 61 | 0.3277 | −21% |
| creatinine | 9 | 0.3292 | −22% |
| phosphate | 50 | 0.3295 | −19% |
| Isobar-36-includes-D-sorbitol-6-phosphate-mannitol-1-phosphate | 61 | 0.3299 | 37% |
| 4-methyl-2-oxopentanoate | 50 | 0.3307 | 30% |
| n-hexadecanoic acid | 50 | 0.3351 | −18% |
| hippuric acid | 61 | 0.339 | −32% |
| glutamine | 61 | 0.3424 | 13% |
| alpha-keto-glutarate | 61 | 0.3442 | 53% |
| tyramine | 50 | 0.3471 | 23% |
| hydroxyacetic acid | 50 | 0.3522 | 12% |
| aspartate | 9 | 0.3546 | −26% |
| serine | 50 | 0.3632 | 19% |
| L-arabitol-adonitol | 50 | 0.3642 | −13% |
| 3-methyl-L-histidine | 61 | 0.3657 | −12% |
| D-lyxose | 50 | 0.3722 | 13% |
| valine | 50 | 0.375 | 13% |
| n-dodecanoate | 50 | 0.3827 | −18% |
| 4-Guanidinobutanoic acid | 61 | 0.3918 | −23% |
| tartaric acid | 61 | 0.3943 | −18% |
| benzoic acid | 50 | 0.3948 | −10% |
| arginine | 9 | 0.3987 | −23% |
| normetanephrine | 50 | 0.4063 | 15% |
| oxitryptan | 9 | 0.4184 | −46% |
| glutamine | 50 | 0.4185 | 13% |
| niacinamide | 61 | 0.4192 | 30% |
| 5-6-Dimethylbenzimidazole- | 50 | 0.4197 | 14% |
| heneicosanoic acid-methyl-ester | 50 | 0.422 | 11% |
| phosphopantheine | 61 | 0.4265 | −36% |
| glutamine | 50 | 0.4411 | 19% |
| gamma-L-glutamyl-L-glutamine | 61 | 0.4444 | −26% |
| uridine | 9 | 0.4469 | −17% |
| DL-pipecolic acid | 61 | 0.4559 | −17% |
| glucose-6-phosphate | 50 | 0.468 | 22% |
| DL-pipecolic acid | 9 | 0.4726 | 60% |

TABLE 1-continued

Depression vs. Control

| Compound | Library | p-value | % Change in Depression |
|---|---|---|---|
| glutamic acid | 9 | 0.4778 | −17% |
| ornithine | 50 | 0.4857 | 21% |
| 3-hydroxybutanoic acid | 50 | 0.489 | −21% |
| isoleucine | 50 | 0.5016 | 14% |
| sn-Glycerol-3-phosphate | 50 | 0.5062 | −12% |
| alanine | 50 | 0.5098 | 10% |
| inosine | 61 | 0.5287 | −36% |
| mannose | 50 | 0.5394 | 19% |
| shikimic acid | 50 | 0.5441 | 20% |
| N-5-aminocarbonyl-L-ornithine | 50 | 0.5457 | −13% |
| 3-amino-isobutyrate | 9 | 0.5494 | −13% |
| xanthine | 61 | 0.5502 | −18% |
| heptadecanoic acid | 50 | 0.5573 | −10% |
| inositol | 50 | 0.568 | 19% |
| Isobar-18-includes-D-fructose-1-phosphate-beta-D-fructose-6-phosphate | 61 | 0.5889 | 14% |
| threonine | 50 | 0.5893 | 10% |
| cysteine | 50 | 0.5975 | −12% |
| vitamin-B6 | 50 | 0.6023 | 16% |
| dopamine | 50 | 0.6048 | −11% |
| arachidonic acid | 50 | 0.6114 | −16% |
| adenosine-3-5-cyclic-monophosphate | 61 | 0.6133 | −19% |
| glucose-6-phosphate | 9 | 0.6329 | −13% |
| glucono-gamma-lactone | 50 | 0.6332 | 17% |
| vitamin-B6 | 9 | 0.6355 | −13% |
| fructose | 50 | 0.636 | −14% |
| aspartate | 61 | 0.6449 | 10% |
| Isobar-1-includes-mannose-fructose-glucose-galactose-alpha-L-sorbopyranose-Inositol-D-allose | 61 | 0.6475 | −23% |
| glutamic acid | 50 | 0.6524 | 11% |
| Isobar-35-includes-D-arabinose-5-phosphate-D-ribulose-5-phosphate-alpha-D-ribose-5-phosphate | 61 | 0.6644 | 19% |
| palmitoleic acid | 50 | 0.6648 | −13% |
| 2-3-dihydroxybenzoic acid | 61 | 0.6686 | −14% |
| elaidic acid | 50 | 0.6732 | −10% |
| sorbitol | 61 | 0.6757 | 11% |
| alpha-L-sorbopyranose | 50 | 0.7039 | −11% |
| 2-keto-L-gulonic acid | 50 | 0.7058 | 12% |
| caffeine | 61 | 0.7073 | −17% |
| gulono-1-4-lactone | 9 | 0.7634 | 10% |
| possible D-galactose | 9 | 0.7749 | −10% |
| L-beta-imidazolelactic acid | 50 | 0.7818 | 10% |
| Isobar-13-includes-5-keto-D-gluconic acid-2-keto-L-gulonic acid-D-glucuronic acid | 61 | 0.7822 | 11% |
| Isobar-25-includes-L-gulono-1-4-lactone-glucono-gamma-lactone- | 61 | 0.8182 | −12% |
| 5-hydroxylysine | 61 | 0.8198 | −13% |

TABLE 2

Depressed vs. Remission

| Compound | Library | p-value | % Change in Depression |
|---|---|---|---|
| Metabolite-405 | 9 | 0.0002 | −55% |
| Metabolite-286 | 9 | 0.001 | −55% |
| Metabolite-3017 | 50 | 0.0025 | −56% |
| Metabolite-597 | 9 | 0.003 | −32% |
| Metabolite-511 | 9 | 0.0042 | −22% |
| Metabolite-2812 | 61 | 0.0044 | 50% |
| methyl-indole-3-acetate | 61 | 0.0048 | 34% |
| Metabolite-568 | 9 | 0.005 | −31% |
| Metabolite-420 | 9 | 0.0051 | −35% |
| Metabolite-146 | 9 | 0.0067 | −63% |
| octadecanoic acid | 9 | 0.007 | −30% |
| 3-hydroxybutanoic acid | 9 | 0.0078 | −65% |
| Metabolite-3065 | 50 | 0.0079 | 47% |

TABLE 2-continued

Depressed vs. Remission

| Compound | Library | p-value | % Change in Depression |
|---|---|---|---|
| glycerol | 9 | 0.0112 | −34% |
| pentanedioic acid | 9 | 0.0119 | −39% |
| Metabolite-1979 | 61 | 0.0124 | 37% |
| Metabolite-278 | 9 | 0.0127 | −50% |
| tetradecanoic acid | 9 | 0.013 | −34% |
| Metabolite-223 | 9 | 0.0145 | −26% |
| citric acid | 9 | 0.0146 | −26% |
| Metabolite-2051 | 61 | 0.0152 | −52% |
| dulcitol | 50 | 0.0158 | −56% |
| alpha-Hydroxyisobutyric acid tms- | 9 | 0.0162 | −32% |
| 9,12-octadecadienoic acid z-z | 9 | 0.0179 | −50% |
| palmitoleic acid | 9 | 0.0187 | −45% |
| Metabolite-387 | 9 | 0.0193 | −45% |
| 3-hydroxybutanoic acid | 50 | 0.0207 | −135% |
| Isobar-28-includes-L-threonine-L-allothreonine | 61 | 0.0217 | 22% |
| Metabolite-1975 | 61 | 0.0234 | −154% |
| Metabolite-272 | 9 | 0.0243 | −25% |
| Metabolite-1974 | 61 | 0.0252 | −56% |
| Metabolite-3097 | 50 | 0.0253 | −105% |
| glycerate | 9 | 0.0264 | −32% |
| Metabolite-2347 | 61 | 0.0283 | 63% |
| Metabolite-554 | 9 | 0.0292 | −39% |
| 5-6-Dimethylbenzimidazole- | 50 | 0.0297 | 37% |
| Metabolite-3099 | 50 | 0.0304 | −86% |
| oleic acid | 9 | 0.033 | −46% |
| Metabolite-480 | 9 | 0.0332 | −37% |
| orotidine-5-phosphate | 61 | 0.0335 | 47% |
| palmitate | 9 | 0.0349 | −34% |
| galactose | 50 | 0.0359 | −70% |
| oxitryptan | 61 | 0.0375 | −61% |
| Metabolite-2074 | 61 | 0.0377 | −170% |
| Metabolite-541 | 9 | 0.0388 | 90% |
| Metabolite-1335 | 61 | 0.0389 | −123% |
| Metabolite-3475 | 61 | 0.0395 | 65% |
| pentadecanoic acid-methyl-ester | 50 | 0.0407 | −70% |
| Metabolite-1086 | 61 | 0.0425 | −368% |
| Metabolite-3709 | 61 | 0.0435 | −135% |
| L-alpha-glycerophosphorylcholine | 61 | 0.0449 | 44% |
| Metabolite-2697 | 61 | 0.0456 | −57% |
| Metabolite-688 | 9 | 0.0467 | −43% |
| hydroorotate | 9 | 0.0468 | −15% |
| Metabolite-3783 | 61 | 0.0472 | −38% |
| Metabolite-2548 | 61 | 0.048 | 34% |
| 1-7-dihydro-6h-purin-6-one | 61 | 0.0488 | −92% |
| Metabolite-4586 | 61 | 0.0503 | 44% |
| Metabolite-691 | 9 | 0.0506 | −18% |
| alanine | 50 | 0.0523 | 29% |
| Metabolite-279 | 9 | 0.0534 | −35% |
| glutamic acid | 50 | 0.0536 | 48% |
| Metabolite-702 | 9 | 0.0537 | −38% |
| 4-aminobutanoic acid | 9 | 0.0556 | −39% |
| alpha-L-sorbopyranose | 50 | 0.056 | −80% |
| methyl-stearate | 50 | 0.0577 | −31% |
| Isobar-19-includes-D-saccharic acid-2-deoxy-D-galactose-2-deoxy-D-glucose-L-fucose-L-rhamnose | 61 | 0.0579 | 31% |
| Metabolite-4446 | 61 | 0.0598 | 70% |
| Metabolite-458 | 9 | 0.0602 | −40% |
| Metabolite-3781 | 61 | 0.0625 | −66% |
| alpha-4-dihydroxybenzenepropanoic acid | 9 | 0.0643 | −25% |
| Metabolite-753 | 9 | 0.0656 | −32% |
| Metabolite-285 | 9 | 0.0685 | −45% |
| Metabolite-3093 | 50 | 0.0694 | −106% |
| Metabolite-293-L-Norleucine | 9 | 0.0716 | −31% |
| Metabolite-3334 | 61 | 0.0722 | −29% |
| alpha-aminoadipic acid | 9 | 0.0729 | −26% |
| Metabolite-709 | 9 | 0.0743 | −25% |
| 9-12-octadecadienoic acid-z-z- | 50 | 0.0759 | −40% |
| 2-amino-heptanedioic acid | 9 | 0.077 | −31% |
| Metabolite-1820 | 61 | 0.077 | −60% |
| tartarate | 9 | 0.0772 | −32% |
| Metabolite-3578 | 61 | 0.0829 | −47% |
| gluconic acid | 9 | 0.0847 | −40% |

TABLE 2-continued

Depressed vs. Remission

| Compound | Library | p-value | % Change in Depression |
|---|---|---|---|
| arginine | 9 | 0.0859 | 58% |
| 3-amino-isobutyrate | 9 | 0.0903 | −28% |
| Metabolite-1216 | 61 | 0.0908 | 22% |
| Metabolite-2056 | 61 | 0.0908 | −121% |
| Metabolite-2370 | 61 | 0.0911 | −33% |
| gulono-1-4-lactone | 9 | 0.0915 | −39% |
| octadecanoic acid | 50 | 0.0915 | −24% |
| glutamic acid | 9 | 0.0929 | 46% |
| Metabolite-4362 | 50 | 0.0935 | −79% |
| Metabolite-3401 | 61 | 0.0941 | −93% |
| Metabolite-596 | 9 | 0.0957 | −32% |
| Metabolite-620 | 9 | 0.0957 | −25% |
| 2-keto-L-gulonic acid | 50 | 0.0959 | −68% |
| vitamin-B6 | 9 | 0.0959 | −30% |
| Metabolite-2687 | 61 | 0.0989 | 18% |
| Metabolite-4526 | 61 | 0.0989 | −80% |
| alpha-tocopherol | 9 | 0.0991 | −24% |
| Metabolite-1656 | 61 | 0.0993 | −95% |
| Metabolite-2546 | 61 | 0.1001 | 43% |
| 3-hydroxyphenylacetate | 61 | 0.102 | −15% |
| Metabolite-3033 | 50 | 0.1022 | −31% |
| tetronic acid | 9 | 0.1028 | −30% |
| Metabolite-580 | 9 | 0.1049 | −30% |
| methyl-palmitate | 50 | 0.1055 | −35% |
| uridine | 61 | 0.1056 | −19% |
| xylitol | 61 | 0.1064 | −111% |
| glycerol | 50 | 0.1089 | −33% |
| sorbitol | 61 | 0.109 | 31% |
| N-formyl-L-methionine | 61 | 0.1152 | −50% |
| catechol | 61 | 0.1162 | 56% |
| tetradecanoic acid | 50 | 0.117 | −47% |
| hippuric acid | 61 | 0.1176 | −39% |
| n-hexadecanoic acid | 50 | 0.1205 | −28% |
| Isobar-30-includes-maltotetraose-stachyose | 61 | 0.1216 | −34% |
| asparagine | 50 | 0.123 | 20% |
| succinate | 50 | 0.1256 | 30% |
| taurine | 61 | 0.1263 | 53% |
| n-dodecanoate | 50 | 0.1327 | −64% |
| allantoin | 61 | 0.1368 | −36% |
| glutamine | 50 | 0.1395 | 25% |
| tyramine | 50 | 0.1434 | 35% |
| Isobar-9-includes-sucrose-beta-D-lactose-D-trehalose-D-cellobiose-D-Maltose-palatinose-melibiose-alpha-D-lactose | 61 | 0.1435 | 31% |
| malic acid | 50 | 0.1455 | 32% |
| elaidic acid | 50 | 0.1494 | −63% |
| valine | 50 | 0.1546 | 24% |
| chorismate | 61 | 0.155 | 32% |
| cholesterol | 9 | 0.1592 | −17% |
| picolinic acid | 61 | 0.1612 | 20% |
| ornithine | 50 | 0.1653 | 42% |
| inositol | 50 | 0.1659 | −56% |
| L-beta-imidazolelactic acid | 50 | 0.1681 | −84% |
| glucono-gamma-lactone | 50 | 0.1696 | −71% |
| alpha-4-dihydroxybenzenepropanoic acid | 61 | 0.1704 | 29% |
| heptadecanoic acid | 50 | 0.1718 | −26% |
| mannose | 50 | 0.1778 | −51% |
| glucarate | 9 | 0.1807 | −22% |
| 3-methyl-L-histidine | 61 | 0.1841 | 15% |
| niacinamide | 61 | 0.1885 | 50% |
| fructose | 50 | 0.1896 | 41% |
| glutamine | 50 | 0.1923 | 34% |
| mercaptopyruvate | 61 | 0.1939 | −18% |
| palmitoleic acid | 50 | 0.2061 | −49% |
| uric acid | 50 | 0.2081 | 23% |
| L-histidinol | 61 | 0.2088 | 18% |
| glucose-6-phosphate | 50 | 0.2194 | −39% |
| dopamine | 50 | 0.2226 | 26% |
| vitamin-B6 | 50 | 0.2232 | −55% |
| N-acetyl-L-leucine | 61 | 0.2252 | 32% |
| histidine | 50 | 0.2255 | 17% |
| pantothenic acid | 61 | 0.2268 | −55% |
| anthranilic acid | 50 | 0.2345 | 21% |
| melibiose | 50 | 0.2377 | 51% |
| hydroxyacetic acid | 50 | 0.2411 | 13% |
| tyrosine | 50 | 0.2416 | 24% |
| tryptophan | 9 | 0.2469 | −32% |
| 6-phosphogluconic acid | 61 | 0.2473 | −17% |
| possible-ISOBAR-DL-aspartic acid- | 50 | 0.2493 | 31% |
| ethylmalonic acid | 61 | 0.254 | −45% |
| serine | 50 | 0.2578 | 23% |
| alpha-keto-glutarate | 61 | 0.2635 | 61% |
| aspartate | 61 | 0.2671 | 22% |
| DL-homocysteine | 61 | 0.2706 | 18% |
| proline | 50 | 0.2728 | 37% |
| selenocystine | 61 | 0.2781 | −25% |
| acetylphosphate | 61 | 0.2822 | 27% |
| creatinine | 61 | 0.2833 | 15% |
| aspartate | 9 | 0.2856 | −19% |
| phosphoenolpyruvate | 61 | 0.2891 | −16% |
| riboflavine | 61 | 0.2903 | −50% |
| Isobar-1-includes-mannose-fructose-glucose-galactose-alpha-L-sorbopyranose-Inositol-D-allose | 61 | 0.2921 | −74% |
| lysine | 9 | 0.2949 | 29% |
| glyceraldehyde | 50 | 0.2999 | −25% |
| noradrenaline | 50 | 0.3048 | 24% |
| malonic acid | 61 | 0.3074 | −23% |
| D-lyxose | 50 | 0.3076 | −18% |
| leucine | 50 | 0.3111 | 21% |
| glyceric acid | 50 | 0.3119 | −20% |
| lactate | 50 | 0.315 | 11% |
| alphahydroxybenzeneacetic acid | 61 | 0.3208 | 14% |
| decanoic acid | 9 | 0.3237 | −21% |
| beta-hydroxypyruvic acid | 61 | 0.3415 | −24% |
| normetanephrine | 50 | 0.3445 | 17% |
| shikimic acid | 50 | 0.3521 | −38% |
| 4-methyl-2-oxopentanoate | 50 | 0.3527 | 28% |
| possible n-Butylamine | 9 | 0.3617 | −17% |
| possible D-galactose | 9 | 0.3654 | −22% |
| cytosine | 61 | 0.3682 | −34% |
| alpha-methyl-L-beta-3-4-dihydroxyphenylalanine | 50 | 0.3714 | 12% |
| 2-aminobutanoic acid | 9 | 0.3777 | −17% |
| 2-isopropylmalic acid | 61 | 0.3784 | 11% |
| 1-methyladenine | 50 | 0.3834 | −15% |
| 2-3-dihydroxybenzoic acid | 61 | 0.3837 | −34% |
| N-N-dimethylarginine | 61 | 0.3978 | −15% |
| uridine | 9 | 0.4107 | −11% |
| alpha-tocopherol | 50 | 0.412 | −15% |
| tartaric acid | 61 | 0.4285 | 20% |
| isoleucine | 50 | 0.434 | 17% |
| urea | 9 | 0.4362 | −17% |
| histamine | 61 | 0.4394 | 11% |
| Isobar-25-includes-L-gulono-1-4-lactone-glucono-gamma-lactone- | 61 | 0.4433 | −53% |
| arginino-succinate | 61 | 0.4632 | −15% |
| glycine | 50 | 0.4663 | 16% |
| urea | 50 | 0.4699 | −14% |
| Isobar-13-includes-5-keto-D-gluconic acid-2-keto-L-gulonic acid-D-glucuronic acid | 61 | 0.4826 | −34% |
| threonine | 50 | 0.4939 | 10% |
| phosphopantheine | 61 | 0.4976 | −52% |
| thyroxine | 61 | 0.5041 | −12% |
| Isobar-36-includes-D-sorbitol-6-phosphate-mannitol-1-phosphate | 61 | 0.5061 | 25% |
| 4-hydroxy-2-quinolinecarboxylic acid | 61 | 0.5091 | 12% |
| creatinine-creatine | 50 | 0.5109 | −12% |
| DL-pipecolic acid | 61 | 0.5145 | 16% |
| xanthine | 61 | 0.5152 | −17% |
| L-arabitol-adonitol | 50 | 0.5229 | −10% |
| 3-amino-isobutyrate | 50 | 0.523 | −11% |
| 5-oxoproline | 50 | 0.5253 | 10% |
| D-alanyl-D-alanine | 61 | 0.5429 | −12% |
| proline | 9 | 0.5515 | 13% |
| creatinine | 9 | 0.5541 | −12% |

TABLE 2-continued

Depressed vs. Remission

| Compound | Library | p-value | % Change in Depression |
|---|---|---|---|
| Isobar-4-includes-Gluconic acid-arabinose-D-ribose-L-xylose-D-lyxose | 61 | 0.5545 | −18% |
| Isobar-21-includes-gamma-aminobutyryl-L-histidine-L-anserine | 61 | 0.5672 | −28% |
| glucose-6-phosphate | 9 | 0.573 | −11% |
| guanidineacetic acid | 61 | 0.5929 | −19% |
| DOPA | 50 | 0.6068 | −11% |
| adenosine-3-5-cyclic-monophosphate | 61 | 0.6075 | −21% |
| Isobar-18-includes-D-fructose-1-phosphate-beta-D-fructose-6-phosphate | 61 | 0.6123 | −15% |
| Isobar-35-includes-D-arabinose-5-phosphate-D-ribulose-5-phosphate-alpha-D-ribose-5-phosphate | 61 | 0.649 | −16% |
| glycerate | 61 | 0.6491 | −14% |
| oxitryptan | 9 | 0.6607 | −17% |
| inosine | 61 | 0.6728 | −34% |
| possible sugar5 | 9 | 0.7106 | −12% |
| uric acid | 9 | 0.7151 | −19% |
| DL-pipecolic acid | 9 | 0.7281 | 22% |
| Isobar-31-includes-maltotriose-melezitose | 61 | 0.785 | −10% |
| gamma-L-glutamyl-L-glutamine | 61 | 0.799 | −12% |

TABLE 3

Remission vs. Control

| Compound | Library | p-value | % Change in Remission |
|---|---|---|---|
| selenocystine | 61 | 0.0019 | 42% |
| Metabolite-146 | 9 | 0.0021 | 233% |
| 3-phospho-d-glycerate | 61 | 0.0024 | −39% |
| Metabolite-1829 | 61 | 0.0024 | −32% |
| Metabolite-2781 | 61 | 0.0029 | −64% |
| possible-ISOBAR-DL-aspartic acid- | 50 | 0.0043 | −37% |
| Metabolite-1817 | 61 | 0.0045 | 36% |
| anthranilic acid | 50 | 0.0053 | −23% |
| Metabolite-2051 | 61 | 0.0067 | 35% |
| Metabolite-570 | 9 | 0.0071 | −59% |
| Metabolite-272 | 9 | 0.0074 | 74% |
| Metabolite-3772 | 61 | 0.0088 | −36% |
| Metabolite-4428 | 61 | 0.0103 | −45% |
| Metabolite-1831 | 61 | 0.0116 | −32% |
| fructose | 50 | 0.0125 | −50% |
| inositol | 9 | 0.0128 | −58% |
| Metabolite-3370 | 61 | 0.0136 | −24% |
| Metabolite-4526 | 61 | 0.0143 | 64% |
| Metabolite-3994 | 61 | 0.0154 | 44% |
| Metabolite-541 | 9 | 0.0159 | −128% |
| dulcitol | 50 | 0.0171 | 41% |
| Metabolite-4161 | 61 | 0.0175 | −55% |
| beta-hydroxypyruvic acid | 61 | 0.018 | 48% |
| arginine | 9 | 0.0183 | −94% |
| Metabolite-2249 | 61 | 0.0187 | −32% |
| Metabolite-2100 | 61 | 0.0196 | 33% |
| Metabolite-1713 | 61 | 0.02 | −36% |
| Metabolite-3099 | 50 | 0.0205 | 46% |
| tartaric acid | 61 | 0.0217 | −34% |
| Metabolite-3807 | 61 | 0.022 | −21% |
| Metabolite-1335 | 61 | 0.0222 | 63% |
| 3-nitro-L-tyrosine | 50 | 0.023 | 30% |
| Metabolite-1975 | 61 | 0.0234 | 61% |
| galactose | 50 | 0.0236 | 46% |
| Metabolite-3093 | 50 | 0.0244 | 63% |
| 3-hydroxyphenylacetate | 61 | 0.0255 | 12% |
| Metabolite-2139 | 61 | 0.0272 | −30% |
| riboflavine | 61 | 0.029 | 63% |
| Metabolite-2285 | 61 | 0.0291 | −37% |
| asparagine | 50 | 0.0296 | −23% |
| Metabolite-3245 | 61 | 0.0301 | −57% |

TABLE 3-continued

Remission vs. Control

| Compound | Library | p-value | % Change in Remission |
|---|---|---|---|
| proline | 9 | 0.031 | −45% |
| Isobar 59: N-6-trimethyl-l-lysine, homoarginine | 61 | 0.0311 | −38% |
| dopamine | 50 | 0.0312 | −34% |
| niacinamide | 61 | 0.0316 | −29% |
| glutamic acid | 9 | 0.0318 | −70% |
| carnitine | 61 | 0.0321 | −23% |
| Metabolite-2074 | 61 | 0.0326 | 66% |
| Metabolite-706 | 9 | 0.034 | −54% |
| proline | 50 | 0.0351 | −34% |
| ornithine | 50 | 0.0363 | −27% |
| 3-phospho-l-serine | 9 | 0.0371 | −63% |
| Metabolite-2806 | 61 | 0.0387 | −15% |
| glutamic acid | 50 | 0.0395 | −41% |
| glycerate | 61 | 0.04 | −35% |
| 5-oxoproline | 9 | 0.0412 | −62% |
| pentadecanoic acid-methyl-ester | 50 | 0.0416 | 42% |
| D-lyxose | 50 | 0.0419 | 27% |
| Metabolite-3316 | 61 | 0.0419 | −27% |
| succinate | 50 | 0.0443 | −35% |
| Metabolite-3017 | 50 | 0.0444 | 25% |
| Metabolite-1086 | 61 | 0.0452 | 78% |
| arabinose | 50 | 0.0456 | −26% |
| Isobar-30-includes-maltotetraose-stachyose | 61 | 0.0462 | 32% |
| Metabolite-4163 | 61 | 0.0464 | −46% |
| nonanate | 50 | 0.048 | 11% |
| Metabolite-3832-possible-phenol-sulfate | 61 | 0.0481 | −51% |
| Metabolite-3030 | 50 | 0.0484 | 25% |
| methyl-stearate | 50 | 0.0484 | 24% |
| Metabolite-2687 | 61 | 0.0489 | −25% |
| Metabolite-2563 | 61 | 0.0493 | −39% |
| Metabolite-1820 | 61 | 0.051 | 36% |
| Metabolite-2313 | 61 | 0.0511 | −19% |
| Metabolite-2711 | 61 | 0.0514 | −36% |
| Metabolite-1573 | 61 | 0.0518 | −34% |
| Metabolite-1114 | 61 | 0.0519 | −26% |
| Metabolite-404 | 9 | 0.0522 | −97% |
| Metabolite-4515 | 50 | 0.0544 | −76% |
| lactate | 50 | 0.0548 | −22% |
| Metabolite-688 | 9 | 0.0559 | 88% |
| Metabolite-1333 | 61 | 0.0563 | −44% |
| 3-amino-isobutyrate | 50 | 0.0579 | 24% |
| Metabolite-2546 | 61 | 0.0584 | −48% |
| Metabolite-2391 | 61 | 0.0593 | 22% |
| Metabolite-293-L-Norleucine | 9 | 0.0599 | 57% |
| alpha-4-dihydroxybenzenepropanoic acid | 61 | 0.0611 | −29% |
| Metabolite-763 | 9 | 0.0613 | −41% |
| gulono-1-4-lactone | 9 | 0.0622 | 81% |
| Metabolite-4233 | 61 | 0.0624 | −24% |
| Metabolite-3235 | 61 | 0.0625 | −38% |
| gluconic acid | 9 | 0.0632 | 80% |
| Metabolite-2507 | 61 | 0.0643 | −77% |
| Metabolite-3075 | 50 | 0.065 | 39% |
| Metabolite-4362 | 50 | 0.066 | 50% |
| 5-oxoproline | 50 | 0.0665 | −33% |
| Metabolite-863 | 9 | 0.0671 | −143% |
| glucose-6-phosphate | 50 | 0.068 | 44% |
| Metabolite-760 | 9 | 0.0687 | −25% |
| Metabolite-3097 | 50 | 0.0696 | 42% |
| mannose | 50 | 0.0731 | 47% |
| 3-methyl-L-histidine | 61 | 0.074 | −25% |
| 2-keto-L-gulonic acid | 50 | 0.0744 | 47% |
| 3-hydroxybutanoic acid | 50 | 0.0759 | 46% |
| Metabolite-3708 | 61 | 0.0765 | −60% |
| malic acid | 50 | 0.0767 | −37% |
| inositol | 50 | 0.0769 | 48% |
| Metabolite-4365 | 50 | 0.0774 | 39% |
| Metabolite-2753 | 61 | 0.0783 | −36% |
| Metabolite-1979 | 61 | 0.0802 | −25% |
| Metabolite-3052 | 61 | 0.0813 | 92% |
| Metabolite-3837 | 61 | 0.0816 | −34% |
| Metabolite-1245 | 61 | 0.0823 | 51% |

TABLE 3-continued

Remission vs. Control

| Compound | Library | p-value | % Change in Remission |
|---|---|---|---|
| Metabolite-3951 | 61 | 0.0823 | −21% |
| Metabolite-3893 | 61 | 0.0831 | 21% |
| Metabolite-1216 | 61 | 0.0841 | −27% |
| Metabolite-3102 | 50 | 0.0849 | −21% |
| Metabolite-1977 | 61 | 0.0852 | −28% |
| uridine | 61 | 0.0857 | 18% |
| Metabolite-1498 | 61 | 0.0864 | −41% |
| Metabolite-687 | 9 | 0.0878 | −47% |
| Metabolite-4196 | 50 | 0.0883 | 32% |
| lysine | 9 | 0.0886 | −36% |
| Metabolite-2347 | 61 | 0.0889 | −68% |
| Metabolite-4361 | 50 | 0.0904 | 23% |
| Metabolite-3475 | 61 | 0.0912 | −49% |
| Metabolite-2567 | 61 | 0.0919 | −43% |
| Metabolite-565 | 9 | 0.092 | −46% |
| catechol | 61 | 0.0921 | −79% |
| Metabolite-4503 | 50 | 0.0936 | −50% |
| alpha-L-sorbopyranose | 50 | 0.0951 | 37% |
| ethylmalonic acid | 61 | 0.0953 | 44% |
| Metabolite-596 | 9 | 0.0954 | 52% |
| Metabolite-4546 | 61 | 0.0964 | −42% |
| Metabolite-3215 | 61 | 0.0966 | −23% |
| Isobar-2-includes-3-amino-isobutyrate-2-amino-butyrate-4-aminobutanoic acid-dimethylglycine-choline- | 61 | 0.0968 | −19% |
| Metabolite-3125 | 61 | 0.0976 | −13% |
| trans-4-hydroxyproline | 50 | 0.0981 | −28% |
| 4-Guanidinobutanoic acid | 61 | 0.0987 | −31% |
| Metabolite-4360 | 50 | 0.099 | −95% |
| Metabolite-3090 | 50 | 0.0998 | 21% |
| Metabolite-270 | 9 | 0.0999 | −324% |
| Metabolite-594 | 9 | 0.1002 | 52% |
| glucono-gamma-lactone | 50 | 0.1028 | 51% |
| alanine | 50 | 0.1032 | −21% |
| glutamine | 50 | 0.104 | −18% |
| Isobar-19-includes-D-saccharic acid-2-deoxy-D-galactose-2-deoxy-D-glucose-L-fucose-L-rhamnose | 61 | 0.1068 | −26% |
| DL-pipecolic acid | 61 | 0.1144 | −30% |
| N-N-dimethylarginine | 61 | 0.1171 | −20% |
| alpha-4-dihydroxybenzenepropanoic acid | 9 | 0.1197 | 38% |
| 3-hydroxybutanoic acid | 9 | 0.1206 | 71% |
| alanine | 9 | 0.1219 | −23% |
| guanosine-5-diphosphate | 61 | 0.1234 | −24% |
| xylitol | 61 | 0.1269 | 49% |
| vitamin-B6 | 50 | 0.1273 | 46% |
| guanidineacetic acid | 61 | 0.1383 | −28% |
| glucarate | 9 | 0.1403 | −28% |
| L-beta-imidazolelactic acid | 50 | 0.143 | 51% |
| cytosine | 61 | 0.1468 | 43% |
| pantothenic acid | 61 | 0.1486 | 37% |
| octopamine | 50 | 0.1495 | 15% |
| inosine | 9 | 0.1553 | −21% |
| leucine | 50 | 0.1672 | −15% |
| methyl-palmitate | 50 | 0.177 | 20% |
| phosphate | 50 | 0.1781 | −22% |
| shikimic acid | 50 | 0.1825 | 42% |
| creatinine | 61 | 0.1826 | −15% |
| 3-amino-isobutyrate | 9 | 0.1882 | 23% |
| tyramine | 50 | 0.1885 | −17% |
| phenylalanine | 9 | 0.1912 | −14% |
| serine | 9 | 0.192 | −17% |
| glutamine | 50 | 0.1983 | −13% |
| methyl-indole-3-acetate | 61 | 0.2026 | −22% |
| 5-6-Dimethylbenzimidazole | 50 | 0.2045 | −26% |
| arginino-succinate | 61 | 0.2046 | 27% |
| N-5-aminocarbonyl-L-ornithine | 50 | 0.2106 | −20% |
| uric acid | 50 | 0.216 | −19% |
| allantoin | 61 | 0.2221 | 23% |
| orotidine-5-phosphate | 61 | 0.2296 | −30% |
| Isobar-18-includes-D-fructose-1-phosphate-beta-D-fructose-6-phosphate | 61 | 0.2325 | 25% |
| N-acetyl-L-leucine | 61 | 0.2368 | −28% |
| tyrosine | 50 | 0.2401 | −18% |
| glyceraldehyde | 50 | 0.2414 | 25% |
| L-histidinol | 61 | 0.2461 | −17% |
| alphahydroxybenzeneacetic acid | 61 | 0.2471 | −14% |
| DL-pipecolic acid | 9 | 0.2507 | 31% |
| noradrenaline | 50 | 0.2526 | −22% |
| biliverdin | 61 | 0.2611 | 26% |
| elaidic acid | 50 | 0.2638 | 31% |
| Isobar-13-includes-5-keto-D-gluconic acid-2-keto-L-gulonic acid-D-glucuronic acid | 61 | 0.2869 | 34% |
| alpha-methyl-L-beta-3-4-dihydroxyphenylalanine | 50 | 0.291 | 14% |
| sn-Glycerol-3-phosphate | 50 | 0.2912 | −18% |
| valine | 50 | 0.2916 | −12% |
| octadecanoic acid | 9 | 0.295 | −30% |
| L-alpha-glycerophosphorylcholine | 61 | 0.2961 | −21% |
| DL-homocysteine | 61 | 0.2976 | 12% |
| DOPA | 50 | 0.2983 | −23% |
| tryptophan | 61 | 0.3013 | 10% |
| vitamin-B6 | 9 | 0.3016 | 26% |
| glycerate | 9 | 0.3019 | −15% |
| histamine | 61 | 0.3022 | 14% |
| palmitate | 9 | 0.3043 | −37% |
| possible n-Butylamine | 9 | 0.3046 | −26% |
| D-alanyl-D-alanine | 61 | 0.3049 | −19% |
| melibiose | 50 | 0.3218 | 35% |
| heptanedioic acid | 61 | 0.3239 | −22% |
| 2-aminobutanoic acid | 9 | 0.3255 | −24% |
| Carnosine | 61 | 0.3311 | −16% |
| tetradecanoic acid | 9 | 0.3465 | −45% |
| 6-phosphogluconic acid | 61 | 0.3676 | 12% |
| n-dodecanoate | 50 | 0.3691 | 25% |
| 4-hydroxy-2-quinolinecarboxylic acid | 61 | 0.3728 | −12% |
| Isobar-28-includes-L-threonine-L-allothreonine | 61 | 0.3894 | −14% |
| urea | 9 | 0.3929 | −17% |
| Isobar-35-includes-D-arabinose-5-phosphate-D-ribulose-5-phosphate-alpha-D-ribose-5-phosphate | 61 | 0.399 | 30% |
| pyridoxamine-phosphate | 61 | 0.4067 | −24% |
| 1-methyladenine | 50 | 0.4166 | 15% |
| alpha-tocopherol | 50 | 0.4171 | −28% |
| uric acid | 9 | 0.4332 | −65% |
| taurine | 61 | 0.439 | −22% |
| acetylphosphate | 61 | 0.4525 | −20% |
| 4-aminobutanoic acid | 9 | 0.4526 | −16% |
| 9,12-octadecadienoic acid z-z | 9 | 0.4538 | −23% |
| tetronic acid | 9 | 0.4543 | −12% |
| melatonin | 50 | 0.4562 | 10% |
| cysteine | 50 | 0.4632 | −16% |
| sorbitol | 61 | 0.4645 | −23% |
| tyrosine | 9 | 0.4733 | −16% |
| gluconic acid | 50 | 0.4742 | −16% |
| alpha-tocopherol | 9 | 0.4752 | −24% |
| palmitoleic acid | 50 | 0.4753 | 22% |
| heptadecanoic acid | 50 | 0.4859 | 11% |
| urea | 50 | 0.4943 | −12% |
| N-formyl-L-methionine | 61 | 0.5239 | −12% |
| Isobar-4-includes-Gluconic acid-arabinose-D-ribose-L-xylose-D-lyxose | 61 | 0.5401 | −14% |
| oleic acid | 9 | 0.5412 | −21% |
| 1-7-dihydro-6h-purin-6-one | 61 | 0.5639 | 14% |
| possible D-galactose | 9 | 0.5797 | 17% |
| palmitoleic acid | 9 | 0.5891 | −20% |
| Isobar-25-includes-L-gulono-1-4-lactone-glucono-gamma-lactone- | 61 | 0.5951 | 26% |
| Isobar-36-includes-D-sorbitol-6-phosphate-mannitol-1-phosphate | 61 | 0.5974 | 16% |
| L-homoserine-lactone | 61 | 0.605 | −15% |
| aspartate | 61 | 0.6064 | −14% |
| gamma-L-glutamyl-L-glutamine | 61 | 0.607 | −17% |
| Isobar-1-includes-mannose-fructose-glucose-galactose-alpha-L-sorbopyranose-Inositol-D-allose | 61 | 0.6087 | 25% |

TABLE 3-continued

Remission vs. Control

| Compound | Library | p-value | % Change in Remission |
|---|---|---|---|
| tryptophan | 9 | 0.6342 | −22% |
| Isobar-21-includes-gamma-aminobutyryl-L-histidine-L-anserine | 61 | 0.64 | 19% |
| alpha-keto-glutarate | 61 | 0.6579 | −17% |
| arachidonic acid | 50 | 0.6677 | −13% |
| oxitryptan | 9 | 0.6702 | −21% |
| caffeine | 61 | 0.705 | −17% |
| 2-3-dihydroxybenzoic acid | 61 | 0.7254 | 14% |
| inosine | 61 | 0.7854 | −14% |

TABLE 4

Correlation of Normalized Data from Run 1 with Data from Run 2

| COMPOUND | Correlation |
|---|---|
| 3-hydroxybutanoic acid | 0.98 |
| cholesterol | 0.73 |
| isoleucine | 0.73 |
| palmitoleic acid | 0.49 |
| proline | 0.85 |
| 9,12-octadecanoic acid | 0.57 |
| serine | 0.64 |
| 5-oxoproline | 0.94 |
| uric acid | 0.48 |

Example 2

Analytical Characterization of Unnamed Biomarker Compounds

Table 5 below includes analytical characteristics of each of the unnamed metabolites listed in Tables 1, 2 and 3 above. The table includes, for each listed Metabolite, the retention time (RT), retention index (RI), mass, quant mass, and polarity obtained using the analytical methods described above. "Mass" refers to the mass of the C12 isotope of the parent ion used in quantification of the compound. The values for "Quant Mass" give an indication of the analytical method used for quantification: "Y" indicates GC-MS and "1" indicates LC-MS. "Polarity" indicates the polarity of the quantitative ion as being either positive (+) or negative (−).

TABLE 5

Analytical Characteristics of Unnamed Metabolites.

| Compound | RT | RI | MASS | QUANT_MASS | POLARITY |
|---|---|---|---|---|---|
| Metabolite-1086 | 4.56 | 4811.0 | 294.1 | 1 | + |
| Metabolite-1216 | 1.60 | 1631.4 | 343.9 | 1 | − |
| Metabolite-1333 | 3.05 | 3794.0 | 321.9 | 1 | + |
| Metabolite-1465 | 3.45 | 3600.0 | 162.1 | 1 | + |
| Metabolite-1573 | 1.63 | 1669.0 | 170.9 | 1 | − |
| Metabolite-1713 | 2.73 | 3050.0 | 174 | 1 | − |
| Metabolite-1820 | 1.45 | 1626.8 | 342.8 | 1 | − |
| Metabolite-1829 | 1.43 | 1600.0 | 135 | 1 | − |
| Metabolite-1831 | 1.46 | 1638.7 | 209.9 | 1 | − |
| Metabolite-1975 | 5.95 | 6093.0 | 344 | 1 | + |
| Metabolite-1977 | 3.56 | 4060.0 | 260.9 | 1 | + |
| Metabolite-1979 | 1.52 | 1690.3 | 199 | 1 | − |
| Metabolite-2051 | 1.45 | 1634.0 | 309 | 1 | + |
| Metabolite-2074 | 2.24 | 2380.9 | 280.1 | 1 | + |
| Metabolite-2139 | 8.09 | 8500.0 | 218.1 | 1 | + |
| Metabolite-2185 | 9.22 | 9499.4 | 246.2 | 1 | + |
| Metabolite-223 | 9.65 | 1677.7 | 217.1365 | Y | + |
| Metabolite-2279 | 12.38 | 12781.0 | 490.1 | 1 | + |
| Metabolite-2313 | 1.56 | 1685.6 | 352.9 | 1 | − |
| Metabolite-2347 | 13.65 | 14091.0 | 450.1 | 1 | + |
| Metabolite-2391 | 10.14 | 10485.7 | 159.1 | 1 | + |
| Metabolite-2507 | 14.44 | 14843.0 | 481.4 | 1 | − |
| Metabolite-2548 | 5.97 | 6430.0 | 202.9 | 1 | − |
| Metabolite-2563 | 2.18 | 2302.0 | 178.9 | 1 | − |
| Metabolite-263 | 5.35 | 1185 | 215.1779 | Y | + |
| Metabolite-2687 | 1.40 | 1593.0 | 181.1 | 1 | − |
| Metabolite-2697 | 3.77 | 4241.2 | 209.9 | 1 | + |
| Metabolite-270 | 10.87 | 1834.9 | 362.22025 | Y | + |
| Metabolite-2753 | 3.38 | 3750.0 | 147 | 1 | + |
| Metabolite-278 | 9.1 | 1624.2 | 117.074 | Y | + |
| Metabolite-2781 | 10.01 | 10224.6 | 202.2 | 1 | − |
| Metabolite-279 | 10.01 | 1731.2 | 274.17083 | Y | + |
| Metabolite-2812 | 9.88 | 10045.3 | 695.1 | 1 | + |
| Metabolite-286 | 10.49 | 1789 | 217.145 | Y | + |
| Metabolite-3017 | 7.61 | 1541.4 | 246.1 | Y | + |
| Metabolite-3033 | 8.88 | 1689.4 | 116.9 | Y | + |
| Metabolite-3052 | 8.70 | 9035.0 | 426.2 | 1 | + |
| Metabolite-3075 | 10.36 | 1857.9 | 204 | Y | + |
| Metabolite-3085 | 11.04 | 1926.1 | 217 | Y | + |
| Metabolite-3090 | 11.31 | 1955 | 243.1 | Y | + |
| Metabolite-3097 | 11.64 | 1990.4 | 204 | Y | + |
| Metabolite-3102 | 11.99 | 2028.2 | 217.1 | Y | + |
| Metabolite-3215 | 1.67 | 1733.8 | 173.8 | 1 | + |

TABLE 5-continued

Analytical Characteristics of Unnamed Metabolites.

| Compound | RT | RI | MASS | QUANT_MASS | POLARITY |
|---|---|---|---|---|---|
| Metabolite-3235 | 10.54 | 10581.1 | 206 | 1 | + |
| Metabolite-3245 | 2.14 | 2168.3 | 816.7 | 1 | − |
| Metabolite-3334 | 3.15 | 3371.5 | 409 | 1 | + |
| Metabolite-3370 | 8.11 | 8529.1 | 226.2 | 1 | + |
| Metabolite-3401 | 1.73 | 1863.3 | 131.1 | 1 | + |
| Metabolite-3405 | 1.76 | 1929.8 | 239.1 | 1 | + |
| Metabolite-3578 | 1.36 | 1525.2 | 296 | 1 | + |
| Metabolite-3653 | 4.05 | 4500.0 | 144.1 | 1 | + |
| Metabolite-3709 | 1.74 | 1828.2 | 202 | 1 | + |
| Metabolite-3781 | 1.45 | 1544.0 | 262.9 | 1 | + |
| Metabolite-3783 | 1.37 | 1464.0 | 271.1 | 1 | + |
| Metabolite-3807 | 3.00 | 3398.5 | 245 | 1 | + |
| Metabolite-382 | 5.12 | 1106.8 | 221.063 | Y | + |
| Metabolite-3832-possible-phenol-sulfate | 8.73 | 8995.8 | 173 | 1 | − |
| Metabolite-385 | 6.49 | 1256.9 | 210.958 | Y | + |
| Metabolite-386 | 9.3 | 1580.1 | 142.09167 | Y | + |
| Metabolite-387 | 10.68 | 1746.5 | 204.077 | Y | + |
| Metabolite-3893 | 3.39 | 3883.5 | 130.1 | 1 | + |
| Metabolite-3951 | 8.41 | 8705.4 | 367.1 | 1 | + |
| Metabolite-3980 | 8.16 | 8480.4 | 353.1 | 1 | + |
| Metabolite-3994 | 1.63 | 1640.4 | 427 | 1 | + |
| Metabolite-404 | 9.34 | 1584.2 | 227.098 | Y | + |
| Metabolite-4161 | 1.32 | 1414.4 | 264.9 | 1 | + |
| Metabolite-4196 | 12.14 | 2000.4 | 290.2 | Y | + |
| Metabolite-420 | 7.32 | 1350.8 | 189.0595 | Y | + |
| Metabolite-421 | 9.18 | 1567.4 | 243.1755 | Y | + |
| Metabolite-4359 | 9.40 | 9673.0 | 433.1 | 1 | − |
| Metabolite-4360 | 9.15 | 1678.2 | 347.2 | Y | + |
| Metabolite-4361 | 9.40 | 1706.2 | 232.2 | Y | + |
| Metabolite-4362 | 10.02 | 1779.9 | 319.2 | Y | + |
| Metabolite-4365 | 11.05 | 1892.9 | 204 | Y | + |
| Metabolite-442 | 4.11 | 997.9 | 176.06857 | Y | + |
| Metabolite-4428 | 7.92 | 8236.5 | 229.2 | 1 | + |
| Metabolite-4498 | 7.06 | 1434.9 | 103 | Y | + |
| Metabolite-4503 | 8.39 | 1589.0 | 227.2 | Y | + |
| Metabolite-4515 | 10.69 | 1853.7 | 318.1 | Y | + |
| Metabolite-4526 | 8.59 | 8769.3 | 233.1 | 1 | − |
| Metabolite-4546 | 10.21 | 10463.8 | 557 | 1 | − |
| Metabolite-458 | 11.9 | 1897 | 204.089 | Y | + |
| Metabolite-4586 | 7.14 | 7486.6 | 260 | 1 | − |
| Metabolite-462 | 4.13 | 999.6 | 204.07225 | Y | + |
| Metabolite-480 | 12.6 | 1979 | 337.219 | Y | + |
| Metabolite-501 | 5.55 | 1155.4 | 143.0835 | Y | + |
| Metabolite-541 | 10.8 | 1779.6 | 174.108 | Y | + |
| Metabolite-554 | 10.74 | 1771.6 | 221.093 | Y | + |
| Metabolite-568 | 5.82 | 1196.6 | 281.04743 | Y | + |
| Metabolite-570 | 10.47 | 1735.6 | 299.0745 | Y | + |
| Metabolite-580 | 11.62 | 1876.8 | 102.02467 | Y | + |
| Metabolite-594 | 11.51 | 1871.3 | 205.1155 | Y | + |
| Metabolite-595 | 3.8 | 968.8 | 100.00267 | Y | + |
| Metabolite-596 | 11.66 | 1878.8 | 217.115 | Y | + |
| Metabolite-597 | 7.91 | 1439 | 218.11 | Y | + |
| Metabolite-620 | 9.06 | 1576.2 | 334.119 | Y | + |
| Metabolite-651 | 4.55 | 1059.6 | 175.1075 | Y | + |
| Metabolite-653 | 6.57 | 1291 | 192.106 | Y | + |
| Metabolite-656 | 13.76 | 2144.4 | 204.12025 | Y | + |
| Metabolite-687 | 9.26 | 1591.8 | 210.977 | Y | + |
| Metabolite-691 | 10.25 | 1711 | 274.08307 | Y | + |
| Metabolite-702 | 10.83 | 1784 | 218.077 | Y | + |
| Metabolite-704 | 6.51 | 1275.1 | 171.05867 | Y | + |
| Metabolite-706 | 10.55 | 1751.4 | 437.153 | Y | + |
| Metabolite-725 | 6 | 1241.2 | 221.082 | Y | + |
| Metabolite-753 | 7.92 | 1465.7 | 218.1368 | Y | + |
| Metabolite-763 | 8.45 | 1528.5 | 230.13467 | Y | + |
| Metabolite-770 | 6.87 | 1341.4 | 247.075 | Y | + |
| Metabolite-863 | 9.98 | 1675 | 347.16121 | Y | + |
| Metabolite-941 | 11.6 | 1912.5 | 204.1 | Y | + |
| Metabolite-995 | 11.42 | 1890.9 | 305.15178 | Y | + |

While the invention has been described in detail and with reference to specific embodiments thereof, it will be apparent to one skilled in the art that various changes and modifications can be made without departing from the spirit and scope of the invention.

What is claimed is:

1. A method of aiding in diagnosing whether a subject has depression, comprising:
    analyzing a blood sample that was removed from a subject to determine the level(s) of biomarkers for depression in the sample, wherein the biomarkers comprise 3-hydroxybutanoic acid, alpha-hydroxyisobutyric acid, and 4-aminobutanoic acid, and wherein the analysis method for the blood sample is mass spectrometry; and
    comparing the level(s) of the biomarkers in the sample to depression-positive and/or depression-negative reference levels of the biomarkers in order to diagnose whether the subject has depression.

2. The method of claim 1, wherein the depression-negative reference levels of the biomarkers comprise levels of the biomarkers in one or more samples from one or more subjects not having depression and the depression-positive reference levels of the biomarkers comprise levels of the biomarkers in one or more samples from one or more subjects diagnosed with depression.

3. The method of claim 2, wherein differential levels of the biomarkers between the sample and the depression-negative reference levels are indicative of a diagnosis of depression in the subject.

4. The method of claim 2, wherein differential levels of the biomarkers between the sample and the depression-positive reference levels are indicative of a diagnosis of no depression in the subject.

5. The method of claim 2, wherein levels of the biomarkers in the sample corresponding to the depression-positive reference levels are indicative of a diagnosis of depression in the subject.

6. The method of claim 2, wherein levels of the biomarkers in the sample corresponding to the depression-negative reference levels are indicative of a diagnosis of no depression in the subject.

7. The method of claim 1, wherein the biological sample is blood plasma.

8. The method of claim 1, wherein the biomarkers further comprise one or more biomarkers selected from the group consisting of glycerol and one or more fatty acids.

9. The method of claim 8, wherein the fatty acids are selected from the group consisting of stearate, myristate, linoleate, palmitoleate, oleate, palmitate, and pentadecanoate.

10. A method of monitoring progression/regression of depression in a subject comprising:
    analyzing a first biological sample that was removed from a subject to determine the level(s) of biomarkers for depression in the sample, wherein the biomarkers comprise 3-hydroxybutanoic acid and 4-aminobutanoic acid and the first sample is obtained from the subject at a first time point, and wherein the analysis method for the blood sample is mass spectrometry;
    analyzing a second biological sample that was removed from a subject to determine the level(s) of the biomarkers, wherein the second sample is obtained from the subject at a second time point and wherein the analysis method is mass spectrometry; and
    comparing the level(s) of the biomarkers in the first sample to the level(s) of the biomarkers in the second sample in order to monitor the progression/regression of depression in the subject.

11. The method of claim 10, wherein the method further comprises comparing the level(s) of the biomarkers in the first sample, the level(s) of the biomarkers in the second sample, and/or the results of the comparison of the level(s) of the biomarkers in the first and second samples to depression-positive reference levels, depression-negative reference levels, depression-progression-positive reference levels, and/or depression-regression-positive reference levels of the biomarkers.

12. The method of claim 10, wherein the biomarkers further comprise one or more biomarkers selected from the group consisting of glycerol and one or more fatty acids.

13. The method of claim 12, wherein the fatty acids are selected from the group consisting of stearate, myristate, linoleate, palmitoleate, oleate, palmitate, and pentadecanoate.

14. A method of assessing the efficacy of a composition for treating depression comprising:
    analyzing a blood sample removed from a subject having depression and currently or previously being treated with a composition to determine the level(s) of biomarkers for depression, wherein the biomarkers comprise 3-hydroxybutanoic acid and 4-aminobutanoic acid and wherein the analysis method for the blood sample is mass spectrometry; and
    comparing the level(s) of the biomarkers in the sample to (a) levels of the biomarkers in a previously-taken biological sample from the subject, wherein the previously-taken biological sample was obtained from the subject before being treated with the composition, (b) depression-positive reference levels of the biomarkers, (c) depression-negative reference levels of the biomarkers, (d) depression-progression-positive reference levels of the biomarkers, and/or (e) depression-regression-positive reference levels of the biomarkers.

15. The method of claim 14, wherein the biomarkers further comprise one or more biomarkers selected from the group consisting of glycerol and one or more fatty acids.

16. The method of claim 15, wherein the fatty acids are selected from the group consisting of stearate, myristate, linoleate, palmitoleate, oleate, palmitate, and pentadecanoate.

17. A method for assessing the efficacy of a composition in treating depression, comprising:
    analyzing a first blood sample obtained from a subject to determine the level(s) of biomarkers for depression, the first sample obtained from the subject at a first time point, wherein the biomarkers comprise 3-hydroxybutanoic acid and 4-aminobutanoic acid and wherein the analysis method for the blood sample is mass spectrometry;
    administering the composition to the subject;
    analyzing a second biological sample obtained from the subject to determine the level(s) of the biomarkers, wherein the second sample is obtained from the subject at a second time point after administration of the composition and wherein the analysis method is mass spectrometry; and
    comparing the level(s) of the biomarkers in the first sample to the level(s) of the biomarkers in the second sample in order to assess the efficacy of the composition for treating depression.

18. The method of claim 17, wherein the biomarkers further comprise one or more biomarkers selected from the group consisting of glycerol and one or more fatty acids.

* * * * *

UNITED STATES PATENT AND TRADEMARK OFFICE
CERTIFICATE OF CORRECTION

PATENT NO. : 8,394,354 B2
APPLICATION NO. : 12/300000
DATED : March 12, 2013
INVENTOR(S) : Lisa A. Paige et al.

It is certified that error appears in the above-identified patent and that said Letters Patent is hereby corrected as shown below:

In the Specifications

Column 10, line 59, replace "biomarkers in," with --biomarkers in--;

Column 13, line 3, delete "of the two compositions"; and

Column 14, line 3, replace "selected from," with --selected from--.

Signed and Sealed this
Twenty-first Day of May, 2013

Teresa Stanek Rea
*Acting Director of the United States Patent and Trademark Office*

UNITED STATES PATENT AND TRADEMARK OFFICE
CERTIFICATE OF CORRECTION

PATENT NO.        : 8,394,354 B2
APPLICATION NO. : 12/300000
DATED             : March 12, 2013
INVENTOR(S)       : Paige et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 865 days.

Signed and Sealed this

First Day of September, 2015

Michelle K. Lee
*Director of the United States Patent and Trademark Office*